US008492555B2

(12) United States Patent
Abele et al.

(10) Patent No.: US 8,492,555 B2
(45) Date of Patent: Jul. 23, 2013

(54) **SALTS OF ISOBUTYRIC ACID (1 R\*, 2R\*, 4R\*)-2-(2-{[3-(4,7-DIMETHOXY-1 H-BENZOIMIDAZOL-2-YL)-METHYL-AMINO}-ETHYL)-5-PHENYL-BICYCLO [2.2.2]OCT-5-EN-2-YL ESTER**

(75) Inventors: Stefan Abele, Allschwil (CH); Stéphanie Combes, Allschwil (CH); Jacques-Alexis Funel, Allschwil (CH); Kurt Hilpert, Allschwil (CH); Francis Hubler, Allschwil (CH); Katharina Reichenbaecher, Riehen (CH); Dorte Renneberg, Allschwil (CH); Markus Von Raumer, Allschwil (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 76 days.

(21) Appl. No.: 13/125,443

(22) PCT Filed: Oct. 21, 2009

(86) PCT No.: PCT/IB2009/054637
§ 371 (c)(1),
(2), (4) Date: Jun. 2, 2011

(87) PCT Pub. No.: WO2010/046857
PCT Pub. Date: Apr. 29, 2010

(65) Prior Publication Data
US 2011/0263667 A1  Oct. 27, 2011

(30) Foreign Application Priority Data

Oct. 22, 2008  (WO) .................. PCT/IB2008/054351

(51) Int. Cl.
*A61K 31/4184*  (2006.01)
*C07D 235/14*  (2006.01)
(52) U.S. Cl.
USPC ..................................... 548/309.7; 514/394
(58) Field of Classification Search
USPC ....................................................... 548/309.7
See application file for complete search history.

(56) References Cited

U.S. PATENT DOCUMENTS

| | | | |
|---|---|---|---|
| 6,268,377 B1 | 7/2001 | Waldstreicher | |
| 8,202,885 B2 * | 6/2012 | Hilpert et al. | 514/307 |
| 2003/0130330 A1 | 7/2003 | Druzgala et al. | |
| 2011/0039905 A1 * | 2/2011 | Hubler et al. | 514/394 |

FOREIGN PATENT DOCUMENTS

| | | |
|---|---|---|
| WO | WO 2008/132679 | 11/2008 |
| WO | WO 2009/130679 | 10/2009 |
| WO | PCT/IB2009/054637 | 4/2010 |
| WO | WO 2010/046855 | 4/2010 |
| WO | WO 2010/046869 | 4/2010 |

OTHER PUBLICATIONS

Gould, International Journal of Pharmaceutics, 33 (1986), pp. 201-217.*
Kones, Vascular Health and Risk Management, 2010, 6, pp. 749-774.*
Du Souich, P. et al., "Nonlinear kinetics and pharmacologic response to mibefradil", *Clinical Pharmacology Therapeutics*, 2000, 67, pp. 249-257.
Clozel, J.P. et al., "Voltage-Gated T-Type $Ca_{2+}$ Channels and Heart Failure", *Proceedings Associatin American Physicians*, 1999, 111, pp. 429-437.
Honda, M. et al., "Divergent renal vasodilator action of L- and T-type calcium antagonists in vivo", *Journal of Hypertension*, 2001, 19, pp. 2031-2037.
Kligfield, P. et al., "A model of graded ischemia in the isolated perfused rat heart", *Journal of Applied Physiology*, 1976, 40(6) pp. 1004-1008.
Döring, H.J., "The Isolated Perfused Heart According to Langendorff Technique-Function-Application", *Physiologie Bohemoslovaca*, 1990, 39(6), pp. 481-504.
Ramires, F.J.A. et al., "Myocardial Fibrosis Associated with Aldosterone or Angiotensin II Administration: Attenuation by Calcium Channel Blockade", *J. Mol. Cell. Cardiol*, 1998, 30, pp. 475-483.
Remington, "Pharmaceutical Manufacturing", *The Science and Practice of Pharmacy*, 21st Edition, 2005, Part 5, Table of Contents Only Submitted.
Villame J. et al., "Effects of Mibefradil, a T- and L-Type Calcium Channel Blocker, on Cardiac Remodeling in the UM-X7.1 Cardiomyopathic Hamster", *Cardiovascular Drugs and Therapy*, 2011, 15, pp. 41-48.
U.S. Appl. No. 12/667,193, filed Jul. 2, 2008.

* cited by examiner

*Primary Examiner* — Laura L. Stockton
(74) *Attorney, Agent, or Firm* — Hoxie & Associates, LLC

(57) ABSTRACT

The invention relates to crystalline salts of isobutyric acid (1R\*,2R\*,4R\*)-2-(2-{[3-(4,7 -dimethoxy-1H-benzoimidazol-2-yl)-propyl]-methyl-amino}-ethyl)-5-phenyl-bicyclo [2.2.2]oct-5-en-2-yl ester, processes for the preparation thereof, pharmaceutical compositions containing said crystalline salts, and their use as medicaments, especially as calcium channel blockers.

13 Claims, 6 Drawing Sheets

SALTS OF ISOBUTYRIC ACID (1 R*, 2R*, 4R*)-2-(2-{[3-(4,7-DIMETHOXY-1 H-BENZOIMIDAZOL-2-YL)-METHYL-AMINO}-ETHYL)-5-PHENYL-BICYCLO[2.2.2]OCT-5-EN-2-YL ESTER

CROSS REFERENCE TO RELATED APPLICATIONS

This application is a United States Application under 35 U.S.C. 371 claiming benefit of PCT Application No. PCT/IB2009/054637, filed on Oct. 21, 2009, which claims the benefit of PCT Application No. PCT/IB2008/054351, filed on Oct. 22, 2008.

The invention relates to novel crystalline salt forms of isobutyric acid (1R*,2R*,4R*)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester (hereinafter also referred to as "COMPOUND") or enantiomers thereof, processes for the preparation thereof, pharmaceutical compositions containing said crystalline salt forms, and their use as calcium channel blockers in the treatment or prevention of chronic stable angina, hypertension, ischemia (renal and cardiac), cardiac arrhythmias including atrial fibrillation, cardiac hypertrophy, or congestive heart failure. Said crystalline salt forms of the present invention may also be used, alone or in pharmaceutical compositions, for the treatment of renal diseases, diabetes and its complications, hyperaldosteronism, epilepsy, neuropathic pain, or cancer in humans and other mammals.

BACKGROUND OF THE INVENTION

Many cardiovascular disorders have been associated with a 'calcium overload' resulting from an abnormal elevated calcium influx through the plasma membrane of cardiac and vascular smooth muscle cells. There are 3 major pathways through which extracellular calcium can enter these cells: 1) receptor-activated calcium channels, 2) ligand-gated calcium channels and 3) voltage-operated calcium channels (VOCs).

VOCs have been classified into 6 main categories: L (Long-lasting), T (Transient), N (Neuronal), P (Purkinje cells), Q (after P) and R (Remaining or Resistant).

L-type calcium channels are responsible for the inward movement of calcium that initiates contraction in cardiac and smooth muscle cells suggesting a putative application for blockers of these channels in the cardiovascular field. In this view, L-type calcium channel blockers have been used in clinic since the early 60 s and are now recommended as a first line of treatment for systolic-diastolic hypertension and angina pectoris.

T-type calcium channels are found in various tissues such as coronary and peripheral vasculature, sinoatrial node and Purkinje fibres, brain, adrenal glands and in the kidney. This broad distribution suggests a T-type channel blocker to have a putative cardiovascular protection, to have en effect on sleep disorders, mood disorders, depression, migraine, hyperaldosteroneemia, preterm labor, urinary incontinence, brain aging or neurodegenerative disorders such as Alzheimers disease.

Mibefradil (Posicor®), the first L-type and T-type calcium channels blocker demonstrated a superior effect over calcium channel blockers, which target the L channel predominantly.

Mibefradil was used for the treatment of hypertension and angina without showing negative side-effects often seen by L channel blockers like inotropy, reflex tachycardia, vasoconstrictive hormone release or peripheral edema. Additionally, mibefradil showed a potentially cardioprotective effect (Villame, Cardiovascular Drugs and Therapy 15, 41-28, 2001; Ramires, J Mol Cell Cardiol 1998, 30, 475-83), a renal protective effect (Honda, Hypertension 19, 2031-37, 2001), and showed a positive effect in the treatment of heart failure (Clozel, Proceedings Association American Physicians 1999, 111, 429-37).

Despite the enormous demand for a compound of this profile, mibefradil was withdrawn from the market in 1998 (one year after its launch), due to unacceptable CYP 3A4 drug interactions. Moreover, ECG abnormalities (i.e. QT prolongations) and interaction with the MDR-1 mediated digoxin efflux were also reported (du Souich, Clin Pharmacol Ther 67, 249-57, 2000; Wandel, Drug Metab Dispos 2000, 28, 895-8).

It has now been found that crystalline salt forms of COMPOUND (isobutyric acid (1R*,2R*,4R*)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester) may under certain conditions be found. Said crystalline salt forms of COMPOUND are novel and may have advantageous properties, especially compared to the free base (WO2008/132679) or the di-hydrochloride salt of COMPOUND. Such advantages may include better flow properties, better solubility, less hygroscopicity, better reproducibiliy in manufacturing (for example better filtration parameters, better reproducibility of formation, better sedimentation), defined morphology and/or better long term stability.

Figure 1:
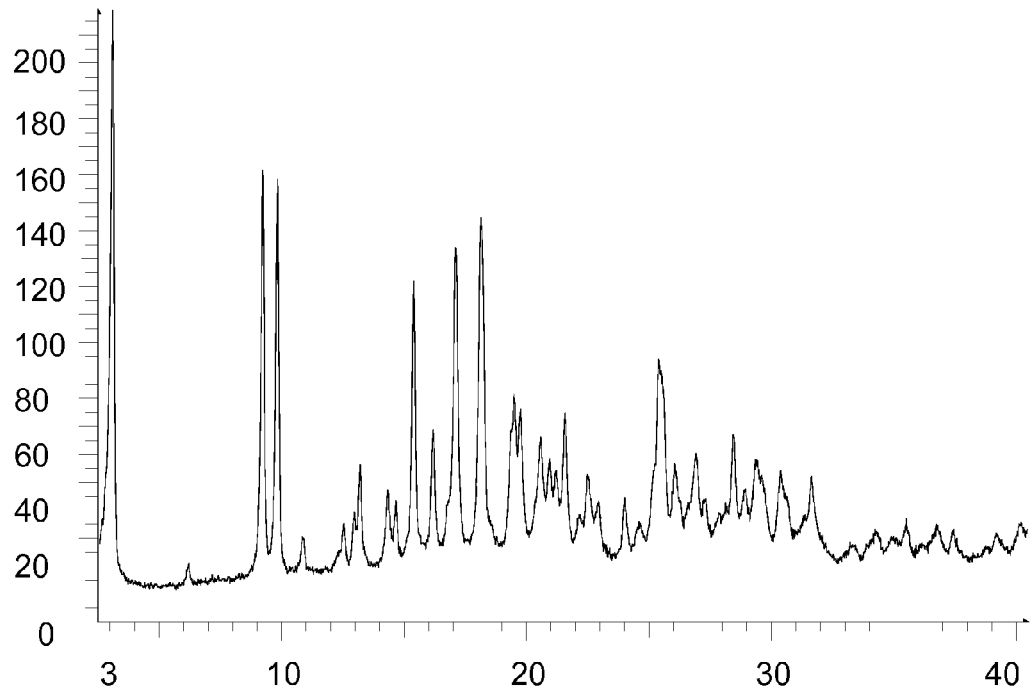
FIG. 1 shows the X-ray powder diffraction diagram of the di-hydrochloric acid salt of COMPOUND in a crystalline form as obtained from Reference Example S1. The X-ray diffraction diagram measured with method 1 shows peaks having a relative intensity, as compared to the most intense peak in the diagram, of the following percentages (relative peak intensitites given in parenthesis) at the indicated angles of refraction 2theta (2θ) (selected peaks from the range 2-40°, 2theta with relative intensity larger then 10% are reported): 3.02° (100%), 9.19° (88%), 9.77° (81%), 10.81° (16%), 12.50° (19%), 12.94° (21%), 13.15° (30%), 14.30° (26%), 14.62° (24%), 15.36° (66%), 16.14° (37%), 17.08° (73%), 18.12° (76%), 19.46° (45%), 19.71° (40%), 20.54° (35%), 20.92° (31%), 21.17° (29%), 21.56° (41%), 22.47° (29%), 22.90° (22%), 23.99° (24%), 25.41° (52%), 26.05° (31%), 26.90° (32%), 27.28° (24%), and 28.45° (37%).

In the X-ray diffraction diagrams of FIG. 1 to FIG. 11 the angle of refraction 2theta (2θ) is plotted on the horizontal axis and the counts on the vertical axis.

DETAILED DESCRIPTION OF THE INVENTION

1) The invention relates to a crystalline salt, especially an essentially pure crystalline salt, of COMPOUND (isobutyric acid (1R*,2R*,4R*)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester); wherein said crystalline salt consists of:
   1 equivalent of COMPOUND;
   an acid component consisting of 1 to 2 equivalents of an acid selected from the group consisting of hydrobromic acid, sulfuric acid, maleic acid, fumaric acid, methanesulfonic acid, para-toluenesulfonic acid, benzenesulfonic acid, naphthalene-1,5-disulfonic acid, naphthalene-2-sulfonic acid, and ethanesulfonic acid; and
   0 to 5 equivalents of water.

2) Another embodiment relates to a crystalline salt of COMPOUND according to embodiment 1), wherein COMPOUND is enantiomerically enriched isobutyric acid (1R, 2R,4R)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester.

3) Another embodiment relates to a crystalline salt of COMPOUND according to embodiment 1), wherein COMPOUND is enantiomerically enriched isobutyric acid (1S,2S,4S)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester.

4) Another embodiment relates to a crystalline salt of COMPOUND according to embodiment 1), wherein COMPOUND is isobutyric acid (1R*,2R*,4R*)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester in enantiomerically enriched form having negative optical rotation.

5) Another embodiment relates to a crystalline salt of COMPOUND according to any one of embodiments 1) to 4), wherein said crystalline salt contains 0 to 3 (especially 0.5 to 3, notably 1 to 2) equivalents of water.

6) Another embodiment relates to a crystalline salt of COMPOUND according to any one of embodiments 1) to 4), wherein said crystalline salt contains 0 equivalents of water.

7) Another embodiment relates to a crystalline salt of COMPOUND according to any one of embodiments 1) to 6), wherein the acid component of said crystalline salt consists of 1 or 2 (especially 2) equivalents of hydrobromic acid, 1 or 2 equivalents of sulfuric acid, 1 or 2 (especially 2) equivalents of maleic acid, 1 to 2 (especially 1.5) equivalents of fumaric acid, 1 or 2 (especially 2) equivalents of methanesulfonic acid, 1 or 2 (especially 2) equivalents of para-toluenesulfonic acid, 1 or 2 (especially 2) equivalents of benzenesulfonic acid, 1 to 2 (especially 1.5) equivalents of naphthalene-1,5-disulfonic acid, 1 or 2 (especially 2) equivalents of naphthalene-2-sulfonic acid, or 1 or 2 (especially 2) equivalents of ethanesulfonic acid.

In a sub-embodiment, the acid component of said crystalline salt preferably consists of 2 equivalents of hydrobromic acid, 1 or 2 equivalents of sulfuric acid, 2 equivalents of maleic acid, 1 to 2 (especially 1.5) equivalents of fumaric acid, 2 equivalents of methanesulfonic acid, 2 equivalents of para-toluenesulfonic acid, or 2 equivalents of benzenesulfonic acid. In another sub-embodiment, the acid component of said crystalline salt preferably consists of 1 or 2 (especially 2) equivalents of maleic acid, or 1 to 2 (especially 1.5) equivalents of fumaric acid.

8) Another embodiment relates to a crystalline salt of COMPOUND according to any one of embodiments 1) to 7), wherein the acid component of said crystalline salt consists of 2 equivalents of hydrobromic acid. A sub-embodiment relates to a crystalline salt of COMPOUND according to any one of embodiments 1) to 5) or 7), wherein the acid component of said crystalline salt consists of 2 equivalents of hydrobromic acid; and wherein said crystalline salt contains about 3 equivalents of water.

9) Another embodiment relates to a crystalline salt of COMPOUND according to any one of embodiments 1) to 7), wherein the acid component of said crystalline salt consists of 1 or 2 equivalents of sulfuric acid.

10) Another embodiment relates to a crystalline salt of COMPOUND according to any one of embodiments 1) to 7), wherein the acid component of said crystalline salt consists of 2 equivalents of maleic acid.

11) Another embodiment relates to a crystalline salt of COMPOUND according to any one of embodiments 1) to 7), wherein the acid component of said crystalline salt consists of 1 to 2 (especially 1.5) equivalents of fumaric acid.

12) Another embodiment relates to a crystalline salt of COMPOUND according to any one of embodiments 1) to 7), wherein the acid component of said crystalline salt consists of 2 equivalents of methanesulfonic acid.

13) Another embodiment relates to a crystalline salt of COMPOUND according to any one of embodiments 1) to 7), wherein the acid component of said crystalline salt consists of 2 equivalents of para-toluenesulfonic acid.

14) Another embodiment relates to a crystalline salt of COMPOUND according to any one of embodiments 1) to 7), wherein the acid component of said crystalline salt consists of 2 equivalents of benzenesulfonic acid.

15) Another embodiment relates to a crystalline salt of COMPOUND according to any one of embodiments 1) to 7), wherein the acid component of said crystalline salt consists of 1 to 2 (especially 1.5) equivalents of naphthalene-1,5-disulfonic acid.

16) Another embodiment relates to a crystalline salt of COMPOUND according to any one of embodiments 1) to 7), wherein the acid component of said crystalline salt consists of 2 equivalents of naphthalene-2-sulfonic acid.

17) Another embodiment relates to a crystalline salt of COMPOUND according to any one of embodiments 1) to 7), wherein the acid component of said crystalline salt consists of 2 equivalents of ethanesulfonic acid.

18) Another embodiment relates to a crystalline salt, especially an essentially pure crystalline salt, of COMPOUND according to embodiment 1) or 10), wherein said crystalline salt consists of:
    1 equivalent of COMPOUND, or of enantiomerically enriched COMPOUND as defined in any one of embodiments 2) to 4);
    2 equivalents of maleic acid; and
    0 equivalents of water.

19) Another embodiment relates to a crystalline salt of COMPOUND according to embodiment 10) or 18), characterised by the presence of peaks in the X-ray powder diffraction diagram at the following angles of refraction 2θ: 10.15°, 20.39°, and 22.63°.

20) Another embodiment relates to a crystalline salt of COMPOUND according to embodiment 10) or 18), characterised by the presence of peaks in the X-ray powder diffraction diagram at the following angles of refraction 2θ: 5.07°, 8.19°, 10.15°, 15.26°, 17.61°, 20.39°, 22.63°, 23.93°, 24.27°, and 25.61°.

Figure 5:
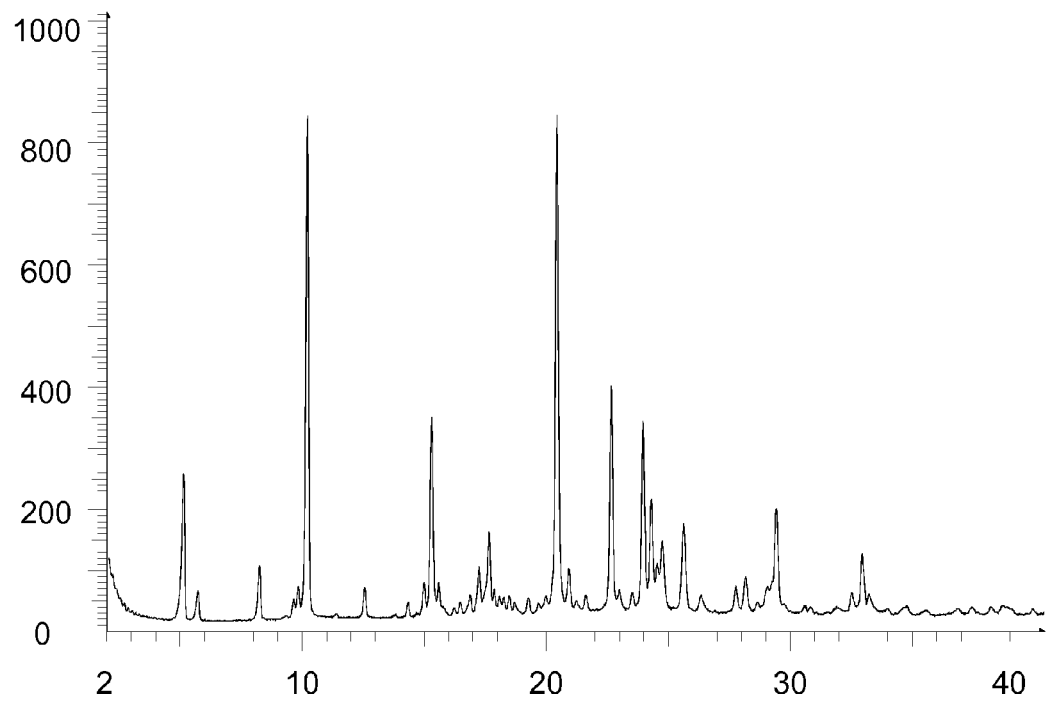
FIG. 5 shows the X-ray powder diffraction diagram of the di-maleic acid salt of COMPOUND in a crystalline form as obtained from Example S5. The X-ray diffraction diagram measured with method 1 shows peaks having a relative intensity, as compared to the most intense peak in the diagram, of the following percentages (relative peak intensitites given in parenthesis) at the indicated angles of refraction 2theta (selected peaks from the range 2-40° 2theta with relative intensity larger then 10% are reported): 5.07° (26%), 8.19° (12%), 10.15° (93%), 15.26° (39%), 17.20° (12%), 17.61° (18%), 20.39° (100%), 20.88° (12%), 22.63° (47%), 23.93° (43%), 24.27° (26%), 24.51° (13%), 24.73° (17%), 25.61° (21%), 29.42° (25%), and 32.93° (16%)

21) Another embodiment relates to a crystalline salt of COMPOUND according to embodiment 10) or 18), which essentially shows the X-ray powder diffraction pattern as depicted in FIG. 5.

22) Another embodiment relates to a crystalline salt of COMPOUND according to embodiment 10) or 18) to 21), which has a melting point of about 147° C. as determined by differential scanning calorimetry using the method as described herein.

23) In another embodiment the present invention relates to a crystalline salt according to any one of embodiments 10) or 18) to 22), obtainable by:
    1. refluxing a solution of COMPOUND (682 g, 84% w/w, 1.05 mol) in EtOAc (6.3 L, 11 volumes);
    2. adding maleic acid (256 g, 2.2 mol, 2.1 eq) dissolved in MeOH (630 mL, 1.1 volumes);
    3. stirring the resulting mixture under reflux for 15 minutes and cooling to 65-68° C. within 30 minutes;
    4. optional seeding with 0.04% w/w of seeding crystals;
    5. cooling the mixture to 40° C. within 3 hours;

6. cooling the mixture to 20° C. within 1 hour;
7. filtering the solid under 0.2 bar of nitrogen and rinsing the solid with EtOAc (1500 mL 2.6 volumes); and
8. drying the solid under 1 atmosphere of nitrogen for 24 hours.

24) Another embodiment relates to a crystalline salt of COMPOUND according to embodiment 8), characterised by the presence of peaks in the X-ray powder diffraction diagram at the following angles of refraction 2θ: 9.3°, 15.6°, and 17.3°.

25) Another embodiment relates to a crystalline salt of COMPOUND according to embodiment 8) or 24), characterised by the presence of peaks in the X-ray powder diffraction diagram at the following angles of refraction 2θ: 6.2°, 9.3°, 15.6°, 17.3°, 18.1°, 19.4°, 20.0°, and 22.8°.

Figure 7:
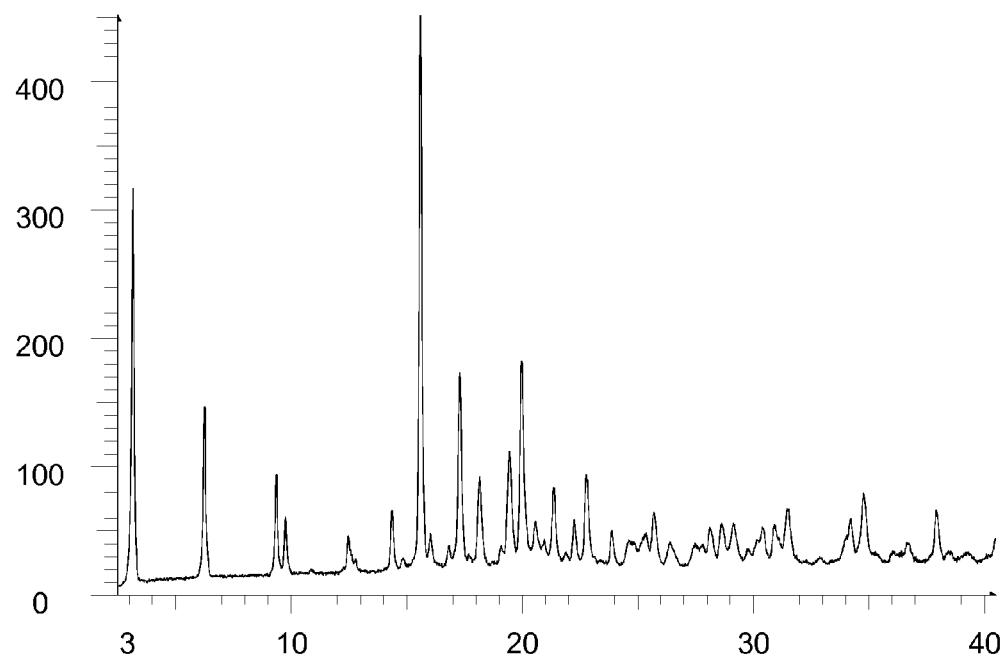
FIG. 7 shows the X-ray powder diffraction diagram of the di-hydrobromic acid salt of COMPOUND in a crystalline form as obtained from Example S7. The X-ray diffraction diagram measured with method 1 shows peaks having a relative intensity, as compared to the most intense peak in the diagram, of the following percentages (relative peak intensitites given in parenthesis) at the indicated angles of refraction 2theta (selected peaks from the range 2-40° 2theta with relative intensity larger then 10% are reported): 3.1° (59%), 6.2° (28%), 9.3° (18%), 14.4° (11%), 15.6° (100%), 17.3° (33%), 18.1° (15%), 19.4° (20%), 20.0° (37%), 21.4° (14%), 22.8° (16%), and 34.8° (43%).

26) Another embodiment relates to a crystalline salt of COMPOUND according to embodiment 8), 24) or 25), which essentially shows the X-ray powder diffraction pattern as depicted in FIG. 7.

27) Another embodiment relates to a crystalline salt of COMPOUND according to embodiment 11), characterised by the presence of peaks in the X-ray powder diffraction diagram at the following angles of refraction 2θ: 5.27°, 8.05°, and 20.61°.

28) Another embodiment relates to a crystalline salt of COMPOUND according to embodiment 11) or 27), characterised by the presence of peaks in the X-ray powder diffraction diagram at the following angles of refraction 2θ: 5.27°, 8.05°, 12.93°, 19.45°, 20.61°, 21.11° and 31.27°.

Figure 6:
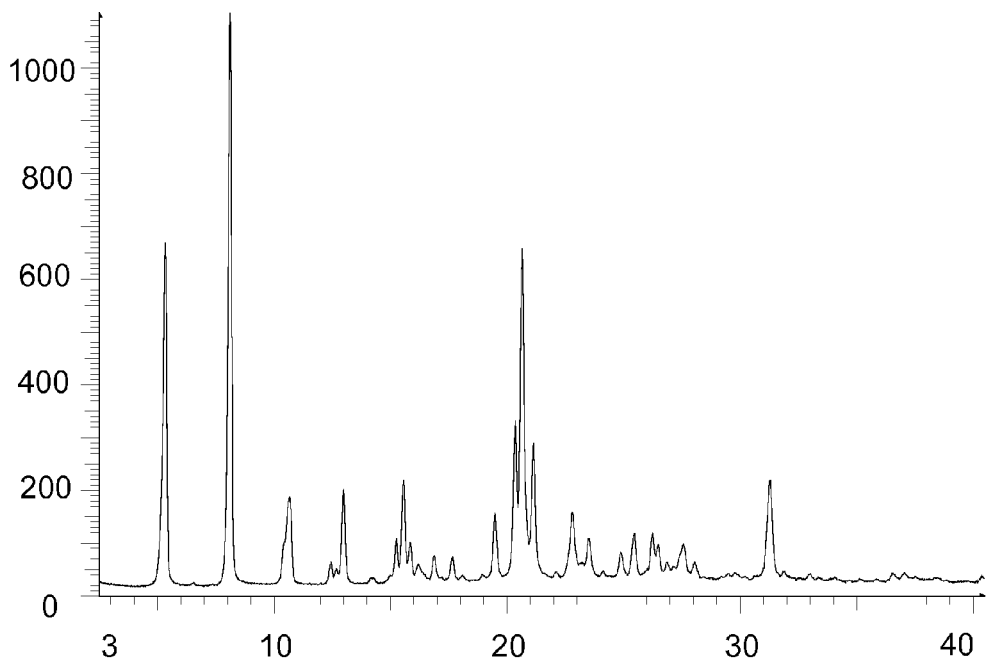
FIG. 6 shows the X-ray powder diffraction diagram of the sesqui-fumaric acid salt of COMPOUND in a crystalline form as obtained from Example S6. The X-ray diffraction diagram measured with method 1 shows peaks having a relative intensity, as compared to the most intense peak in the diagram, of the following percentages (relative peak intensitites given in parenthesis) at the indicated angles of refraction 2theta (selected peaks from the range 2-40° 2theta with relative intensity larger then 10% are reported): 5.27° (57%), 8.05° (100%), 12.93° (18%), 15.20° (10%), 15.50° (20%), 19.45° (14%), 20.31° (31%), 20.61° (62%), 21.11° (27%), 22.77° (15%), 25.42° (11%), 26.22° (11%), and 31.27° (21%).

29) Another embodiment relates to a crystalline salt of COMPOUND according to embodiment 11), 27) or 28), which essentially shows the X-ray powder diffraction pattern as depicted in FIG. 6.

30) Another embodiment relates to a crystalline salt of COMPOUND according to embodiment 11), or 27) to 29), which has a melting point of about 180° C. as determined by differential scanning calorimetry using the method as described herein.

31) Another embodiment relates to a crystalline salt of COMPOUND according to embodiment 12), characterised by the presence of peaks in the X-ray powder diffraction diagram at the following angles of refraction 2θ: 7.21° and 10.00°.

32) Another embodiment relates to a crystalline salt of COMPOUND according to embodiment 12) or 31), characterised by the presence of peaks in the X-ray powder diffraction diagram at the following angles of refraction 2θ: 3.97°, 7.21°, 10.00°, 15.99°, 17.16°, and 21.02°.

Figure 2:
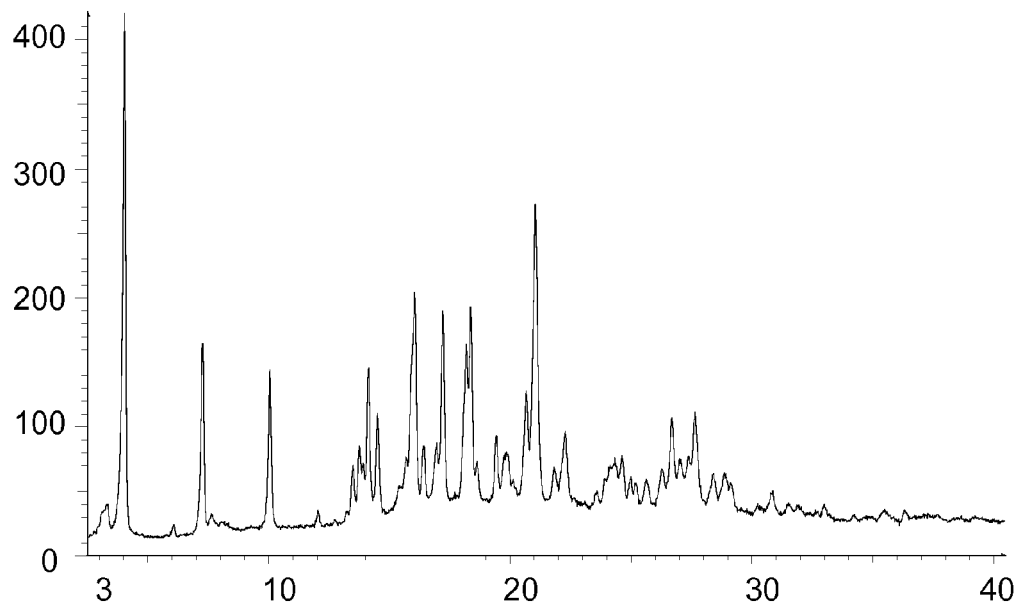
FIG. 2 shows the X-ray powder diffraction diagram of the di-methylsulfonic acid salt of COMPOUND in a crystalline form as obtained from Example S2. The X-ray diffraction diagram measured with method 1 shows peaks having a relative intensity, as compared to the most intense peak in the diagram, of the following percentages (relative peak intensitites given in parenthesis) at the indicated angles of refraction 2theta (selected peaks from the range 2-40° 2theta with relative intensity larger then 10% are reported): 3.97° (100%), 7.21° (42%), 10.00° (39%), 14.09° (40%), 14.45° (29%), 15.99° (55%), 16.38° (22%), 17.16° (51%), 18.12° (44%), 18.34° (53%), 18.60° (19%), 19.38° (25%), 20.62° (35%), 21.02° (74%), 21.79° (18%), 22.24° (25%), 26.66° (30%), and 27.63° (29%).

33) Another embodiment relates to a crystalline salt of COMPOUND according to embodiment 12), 31) or 32), which essentially shows the X-ray powder diffraction pattern as depicted in FIG. 2.

34) Another embodiment relates to a crystalline salt of COMPOUND according to embodiment 13), characterised by the presence of peaks in the X-ray powder diffraction diagram at the following angles of refraction 2θ: 5.79° and 19.84°.

35) Another embodiment relates to a crystalline salt of COMPOUND according to embodiment 13) or 34), characterised by the presence of peaks in the X-ray powder diffraction diagram at the following angles of refraction 2θ: 4.35°, 5.79°, 10.93°, 13.98°, 15.81° and 19.84°.

Figure 3:
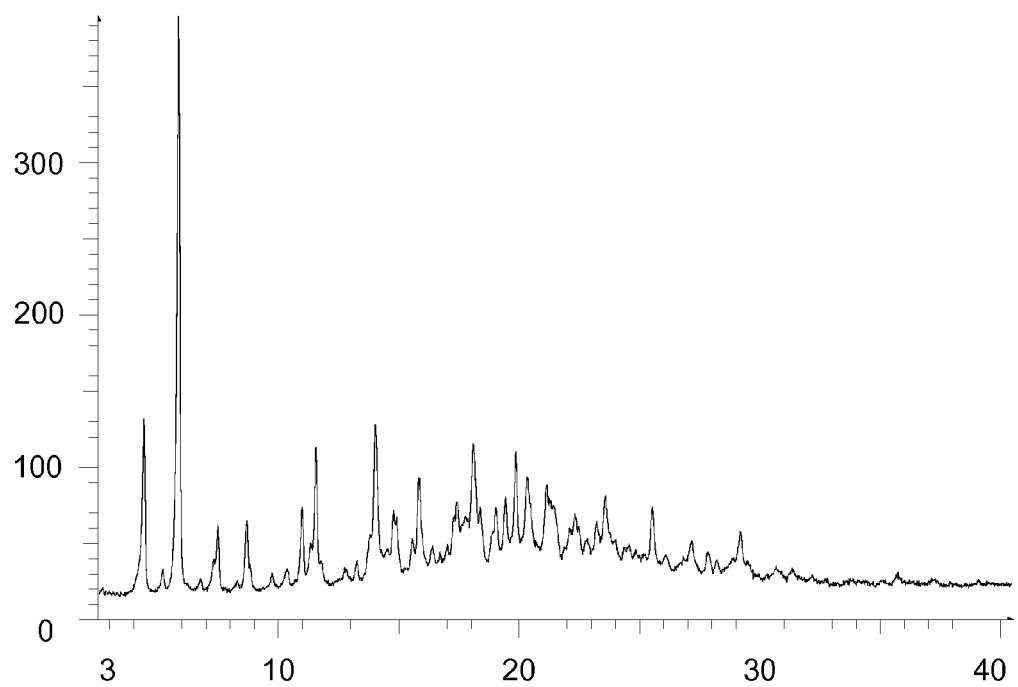
FIG. 3 shows the X-ray powder diffraction diagram of the di-toluenesulfonic acid salt of COMPOUND in a crystalline form as obtained from Example S3. The X-ray diffraction diagram measured with method 1 shows peaks having a relative intensity, as compared to the most intense peak in the diagram, of the following percentages (relative peak intensitites given in parenthesis) at the indicated angles of refraction 2theta (selected peaks from the range 2-40° 2theta with relative intensity larger then 10% are reported): 4.35° (31%), 5.79° (100%), 7.43° (16%), 8.62° (17%), 10.93° (19%), 11.51° (31%), 13.98° (34%), 15.81° (26%), 18.06° (30%), 19.00° (20%), 19.39° (21%), 19.84° (31%), 20.30° (25%), and 25.51° (20%).

36) Another embodiment relates to a crystalline salt of COMPOUND according to embodiment 13), 34) or 35), which essentially shows the X-ray powder diffraction pattern as depicted in FIG. 3.

37) Another embodiment relates to a crystalline salt of COMPOUND according to embodiment 14), characterised by the presence of peaks in the X-ray powder diffraction diagram at the following angles of refraction 2θ: 13.4°, 17.5°, and 21.3°.

38) Another embodiment relates to a crystalline salt of COMPOUND according to embodiment 14) or 37), characterised by the presence of peaks in the X-ray powder diffraction diagram at the following angles of refraction 2θ: 12.6°, 13.4°, 14.7°, 17.5°, 21.3°, and 22.7°.

Figure 9:
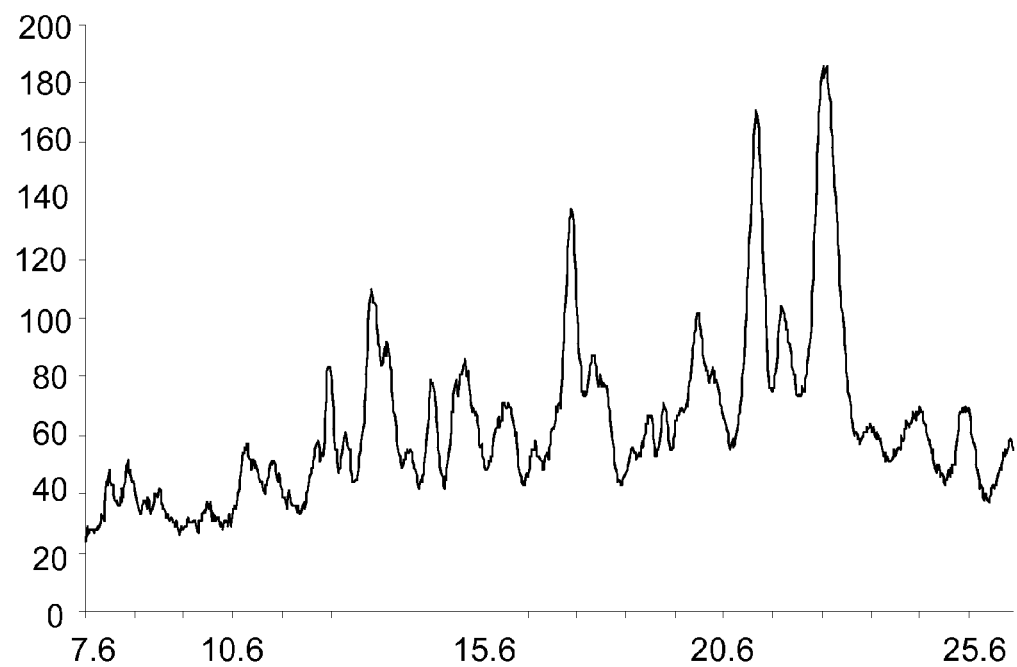
FIG. 9 shows the X-ray powder diffraction diagram of the di-benzenesulfonic acid salt of COMPOUND in a crystalline form as obtained from the general procedure for salt formation. The X-ray diffraction diagram measured with method 2 shows peaks having a relative intensity, as compared to the most intense peak in the diagram, of the following percentages (relative peak intensitites given in parenthesis) at the indicated angles of refraction 2theta (selected peaks from the range 8-26.5° 2theta with relative intensity larger then 10% are reported): 8.1° (16%), 8.5° (18%), 10.9° (20%), 11.4° (16%), 12.3° (20%), 12.6° (37%), 12.9° (22%), 13.4° (55%), 14.6° (32%), 15.3° (37%), 16.1° (27%), 17.5° (71%), 17.9° (37%), 19.1° (22%), 19.4° (25%), 20.1° (46%), 21.3° (91%), 21.8° (46%), 22.7° (100%), 23.6° (18%), 24.5° (20%), and 25.5° (21%).

39) Another embodiment relates to a crystalline salt of COMPOUND according to embodiment 14), 37) or 38), which essentially shows the X-ray powder diffraction pattern as depicted in FIG. 9.

40) Another embodiment relates to a crystalline salt of COMPOUND according to embodiment 15), characterised by the presence of peaks in the X-ray powder diffraction diagram at the following angles of refraction 2θ: 9.9°, 14.2°, and 21.3°.

41) Another embodiment relates to a crystalline salt of COMPOUND according to embodiment 15) or 40), characterised by the presence of peaks in the X-ray powder diffraction diagram at the following angles of refraction 2θ: 9.9°, 12.9°, 14.2°, 20.1°, 20.6°, and 21.3°.

Figure 8:
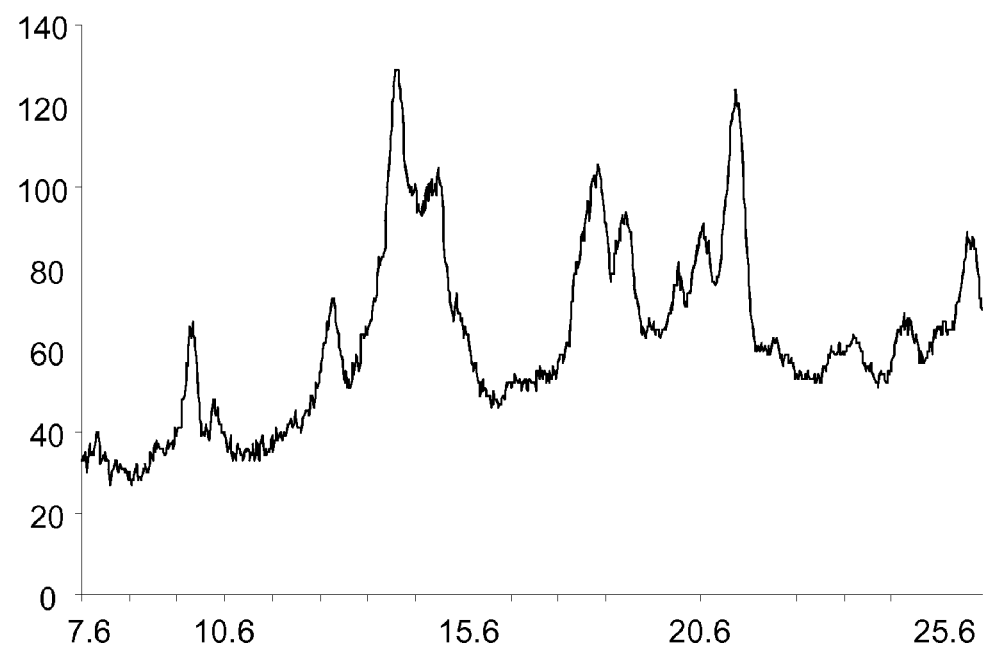
FIG. 8 shows the X-ray powder diffraction diagram of the sesqui-naphthalene-1,5-disulfonic acid salt of COMPOUND in a crystalline form as obtained from the general procedure for salt formation. The X-ray diffraction diagram measured with method 2 shows peaks having a relative intensity, as compared to the most intense peak in the diagram, of the following percentages (relative peak intensitites given in parenthesis) at the indicated angles of refraction 2theta (selected peaks from the range 8-26.5° 2theta with relative intensity larger then 10% are reported): 9.9° (40%), 10.4° (18%), 12.8° (42%), 14.2° (100%), 15.0° (73%), 18.3° (68%), 19° (54%), 20.1° (39%), 20.6° (48%), 21.3° (83%), 23.8° (13%), 24.9° (14%), and 26.2° (22%).

42) Another embodiment relates to a crystalline salt of COMPOUND according to embodiment 15), 40) or 41), which essentially shows the X-ray powder diffraction pattern as depicted in FIG. 8.

43) Another embodiment relates to a crystalline salt of COMPOUND according to embodiment 16), characterised by the presence of peaks in the X-ray powder diffraction diagram at the following angles of refraction 2θ: 9.8°, 11.2°, and 15.6°.

44) Another embodiment relates to a crystalline salt of COMPOUND according to embodiment 16) or 43), characterised by the presence of peaks in the X-ray powder diffraction diagram at the following angles of refraction 2θ: 9.8°, 11.2°, 15.6°, 22.4°, and 23.9°.

Figure 11:
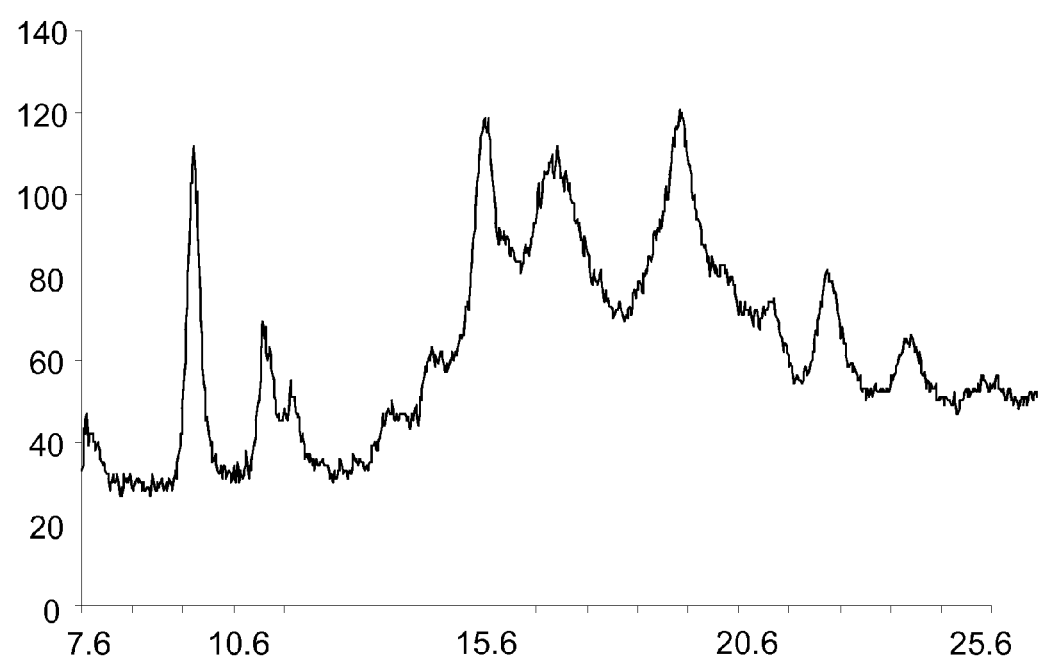
FIG. 11 shows the X-ray powder diffraction diagram of the di-naphthalene-2-sulfonic acid salt of COMPOUND in a crystalline form as obtained from the general procedure for salt formation. The X-ray diffraction diagram measured with method 2 shows peaks having a relative intensity, as compared to the most intense peak in the diagram, of the following percentages (relative peak intensitites given in parenthesis) at the indicated angles of refraction 2theta (selected peaks from the range 8-26.5° 2theta with relative intensity larger then 10% are reported): 9.8° (98%), 11.2° (45%), 11.8° (24%), 13.7° (20%), 14.6° (33%), 15.6° (100%), 16.9° (90%), 19.4° (96%), 22.4° (45%), and 23.9° (23%).

45) Another embodiment relates to a crystalline salt of COMPOUND according to embodiment 16), 43) or 44), which essentially shows the X-ray powder diffraction pattern as depicted in FIG. 11.

46) Another embodiment relates to a crystalline salt of COMPOUND according to embodiment 17), characterised by the presence of peaks in the X-ray powder diffraction diagram at the following angles of refraction 2θ: 11.2°, 15.7°, and 20.4°.

47) Another embodiment relates to a crystalline salt of COMPOUND according to embodiment 17) or 46), characterised by the presence of peaks in the X-ray powder diffraction diagram at the following angles of refraction 2θ: 11.2°, 14.5°, 15.7°, 17.7°, 20.4°, and 22.6°.

Figure 10:
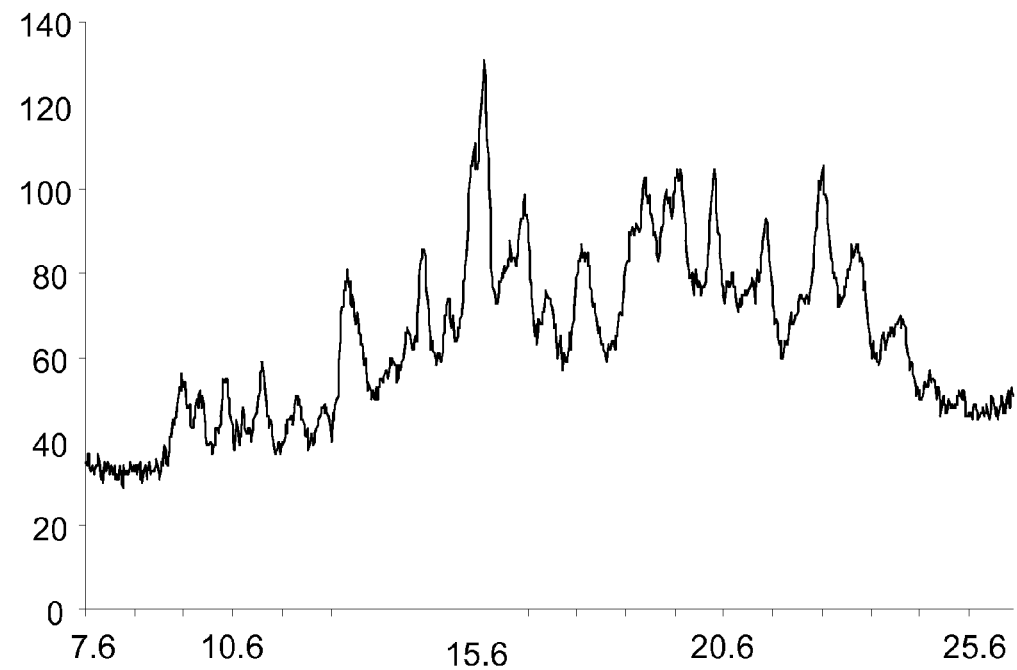
FIG. 10 shows the X-ray powder diffraction diagram of the di-ethanesulfonic acid salt of COMPOUND in a crystalline form as obtained from the general procedure for salt formation. The X-ray diffraction diagram measured with method 2 shows peaks having a relative intensity, as compared to the most intense peak in the diagram, of the following percentages (relative peak intensitites given in parenthesis) at the indicated angles of refraction 2theta (selected peaks from the range 8-26.5° 2theta with relative intensity larger then 10% are reported): 9.6° (25%), 9.9° (21%), 10.5° (23.3%), 11.2° (27%), 11.9° (17%), 12.9° (48%), 14.5° (53%), 15.0° (40%), 15.7° (100%), 16.5° (65%), 17.0° (40%), 17.7° (49%), 19.0° (67%), 19.7° (69%), 20.4° (68%), 21.5° (55%), 22.6° (67%), and 23.3° (47%).

48) Another embodiment relates to a crystalline salt of COMPOUND according to embodiment 17), 46) or 47), which essentially shows the X-ray powder diffraction pattern as depicted in FIG. 10.

49) The invention further relates to a crystalline salt, especially an essentially pure crystalline salt, of COMPOUND (isobutyric acid (1R*,2R*,4R*)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester); wherein said crystalline salt consists of:
1 equivalent of COMPOUND;
an acid component consisting of about 1 equivalent of sulfuric acid; and
about 6 equivalents of water.

50) Another embodiment relates to a crystalline salt of COMPOUND according to embodiment 49), characterised by the presence of peaks in the X-ray powder diffraction diagram at the following angles of refraction 2θ: 11.78°, 13.69°, and 14.19°.

51) Another embodiment relates to a crystalline salt of COMPOUND according to embodiment 49) or 50), characterised by the presence of peaks in the X-ray powder diffraction diagram at the following angles of refraction 2θ: 2.85°, 8.50°, 9.50°, 11.78°, 13.26°, 13.69°, and 14.19°.

Figure 4:
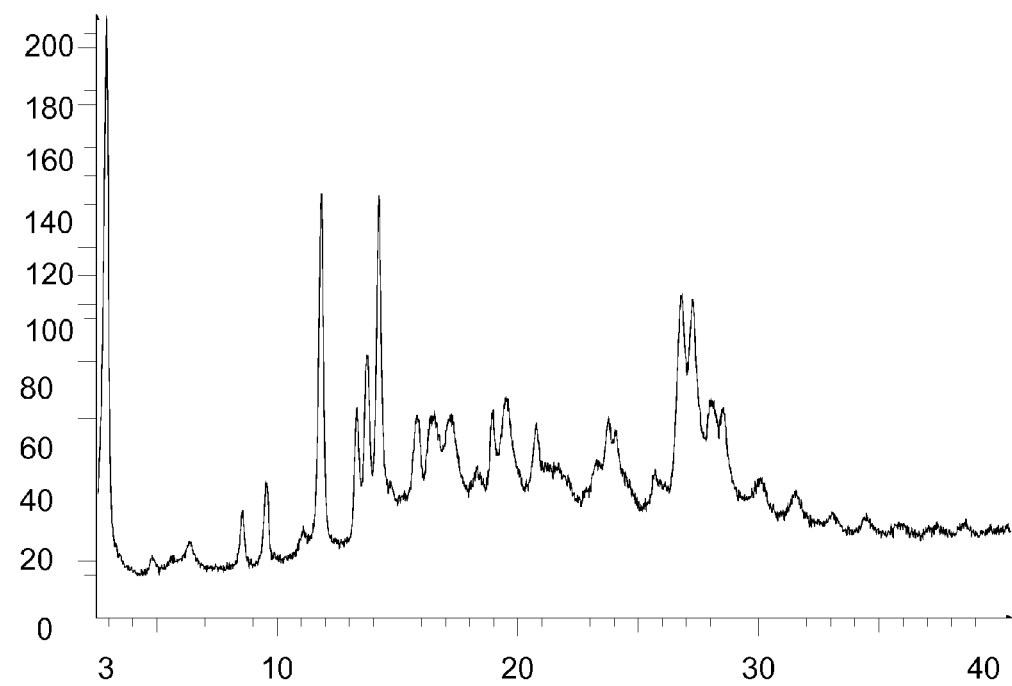
FIG. 4 shows the X-ray powder diffraction diagram of the sulfuric acid salt of COMPOUND in a crystalline form as obtained from Example S4. The X-ray diffraction diagram measured with method 1 shows peaks having a relative intensity, as compared to the most intense peak in the diagram, of the following percentages (relative peak intensitites given in parenthesis) at the indicated angles of refraction 2theta (selected peaks from the range 2-30° 2theta with relative intensity larger then 10% are reported): 2.85° (100%), 8.50° (21%), 9.50° (28%), 11.78° (85%), 13.26° (41%), 13.69° (51%), 14.19° (82%), 15.78° (40%), 16.47° (39%), 17.12° (38%), 18.91° (40%), 19.48° (43%), 26.77° (65%), and 27.24° (63%).

52) Another embodiment relates to a crystalline salt of COMPOUND according to embodiment 49), 50) or 51), which essentially shows the X-ray powder diffraction pattern as depicted in FIG. 4.

For avoidance of any doubt, whenever one of the above embodiments, especially one of embodiments 19), 20), 24), 25), 27), 28), 31), 32), 34), 35), 37), 38), 40), 41), 43), 44), 46), 47), 50) and 51), refers to "peaks in the X-ray powder diffraction diagram at the following angles of refraction 2θ", said X-ray powder diffraction diagram is obtained by using Cu Kα1 radiation (λ=1.5406 Å); and it should be understood that the accuracy of the 2θ values as provided herein is in the range of +/−0.1-0.2°. Notably, when specifying an angle of refraction 2theta (2θ) for a peak in the invention embodiments and the claims, the 2θ value given is to be understood as an interval from said value minus 0.2° to said value plus 0.2° (2θ+/−0.2°); and preferably from said value minus 0.1° to said value plus 0.1° (2θ+/−0.1°).

For avoidance of any doubt, the relative configuration of stereoisomers is denoted as follows:
isobutyric acid (1R*,2R*,4R*)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester denominates
isobutyric acid (1R,2R,4R)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester, or
isobutyric acid (1S,2S,4S)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester,
or mixtures of these two enantiomers such as for example the racemate.

Encompassed in the scope of the present invention are the crystalline salt forms of COMPOUND, i.e. isobutyric acid (1R*,2R*,4R*)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester, described herein; wherein COMPOUND may be in racemic form; in enantiomerically enriched form of the enantiomer of absolute configuration (1R,2R,4R); in enantiomerically enriched form of the enantiomer of absolute configuration (1S,2S,4S); or in form of any mixture of these two enantiomers. Preferred is the enantiomerically enriched form having negative optical rotation as determined using the method as described herein.

Where the plural form is used for compounds, salts, pharmaceutical compositions, diseases and the like, this is intended to mean also a single compound, salt, or the like.

The term "enantiomerically enriched" is understood in the context of the present invention to mean especially that at least 90, preferably at least 95, and most preferably at least 99 per cent by weight of the COMPOUND are present in form of one enantiomer of the COMPOUND.

The term "essentially pure" is understood in the context of the present invention to mean especially that at least 90, preferably at least 95, and most preferably at least 99 per cent by weight of the crystals of a COMPOUND are present in a crystalline form according to the present invention, especially in a single crystalline form of the present invention.

When defining the presence of peak in e.g. an X-ray powder diffraction diagram, a common approach is to do this in terms of the S/N ratio (S=signal, N=noise). According to this definition, when stating that a peak has to be present in an X-ray powder diffraction diagram, it is understood that the peak in the X-ray powder diffraction diagram is defined by having an S/N ratio (S=signal, N=noise) of greater than x (x being a numerical value greater than 1), usually greater than 2, especially greater than 3.

In the context with stating that the crystalline form essentially shows an X-ray powder diffraction pattern as depicted in FIG. 1 to FIG. 11, respectively, the term "essentially" means that at least the major peaks of the diagram depicted in said figures, i.e. those having a relative intensity of more than 10%, especially more than 20%, as compared to the most intense peak in the diagram, have to be present. However, the person skilled in the art of X-ray powder diffraction will recognize that relative intensities in X-ray powder diffraction diagrams may be subject to strong intensity variations due to preferred orientation effects.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C. Room temperature means a temperature of about 25° C. When in the current application the term n equivalent(s) is used wherein n is a number, it is meant and within the scope of the current application that n is referring to about the number n, preferably n is referring to the exact number n.

The crystalline salts, especially the essentially pure crystalline salts, of COMPOUND according to any one of embodiments 1) to 51) can be used as medicaments, e.g. in the form of pharmaceutical compositions for enteral or parenteral administration.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the crystalline forms of the present invention, optionally in combination with other therapeutically valuable substances, into a galenical administration form together with suitable, non-toxic, inert, pharmaceutically acceptable solid or liquid carrier materials and, if desired, usual pharmaceutical adjuvants.

The crystalline salts, especially the essentially pure crystalline salts, of COMPOUND according to any one of embodiments 1) to 51) may be used as single component or as mixtures with other crystalline forms or the amorphous form of COMPOUND.

The crystalline salts, especially the essentially pure crystalline salts, of COMPOUND according to any one of embodiments 1) to 51) are useful in the preparation of a medicament and/or are suitable
  for the treatment or prevention of chronic stable angina, hypertension, ischemia (renal and cardiac), cardiac arrhythmias including atrial fibrillation, cardiac hypertrophy, or congestive heart failure.

The crystalline salts, especially the essentially pure crystalline salts, of COMPOUND according to any one of embodiments 1) to 51) are further also useful in the preparation of a medicament and/or are suitable for the following disease groups alone or in any combination:

- for the treatment of renal diseases, diabetes and its complications, hyperaldosteronism, epilepsy, neuropathic pain, or cancer in humans and other mammals;
- for use as anti-fibrillatory agent, anti-asthmatic agent, anti-atherosclerotic agent, additive to cardioplegic solutions for pulmonary bypasses, adjunct to thrombolytic therapy, as antiaggregant agent, or as agent for the treatment of unstable angina;
- for the treatment or prophylaxis of hypertension, especially portal hypertension, hypertension secondary to treatment with erythropoietin and low renin hypertension;
- for use in hypoxic or ischemic diseases, or as anti ischemic agent for the treatment of e.g. cardiac, renal and cerebral ischemia and reperfusion (e.g. occurring after cardiopulmonary bypass surgery), coronary and cerebral vasospasm and the like, therapy for peripheral vascular diseases (e.g. Raynaud's disease, intermittent claudication, Takayashus disease), sickle cell disease including initiation and/or evolution of the pain crisis;
- for the treatment or prophylaxis of disorders related to renal, glomerular and mesangial cell function, including acute and chronic renal failure, diabetic nephropathy, hypertension-induced nephropathy, glomerular injury, renal damage related to age or dialysis, nephrosclerosis, nephrotoxicity related to imaging and contrast agent and to cyclosporine, renal ischemia, primary vesicoureteral reflux, or glomerulosclerosis;
- for use in therapy for myocardial infarction, treatment of cardiac hypertrophy, primary and secondary pulmonary hypertension, therapy for congestive heart failure including inhibition of fibrosis, inhibition of left ventricular dilatation, remodelling and dysfunction, or restenosis following angioplasty or stenting;
- for the treatment of endotoxemia or endotoxin shock, or hemorrrhagic shock;
- for the treatment of sexual dysfunction in both men (erectile dysfunction e.g. due to diabetes mellitus, spinal cord injury, radical prostatectomy, psychogenic etiology and other causes) and women by improving blood flow to the genitalia, especially corpus cavernosum;
- for the prevention and/or reduction of cancer or end-organ damage associated with cell proliferation;
- for therapy of metabolic disorders or chronic inflammatory diseases, insulin-dependent and non insulin-dependent diabetes mellitus and their complications (e.g. neuropathy, retinopathy), hyperaldosteronism, bone remodelling, psoriasis, arthritis, rheumatoid arthritis, osteoarthritis sarcoidosis, or eczematous dermatitis;
- for the treatment of hepatotoxicity and sudden death, early and advanced liver disease and injury including attendant complication (e.g. hepatotoxicity, fibrosis, cirrhosis), deleterious consequences of tumors such as hypertension resulting from hemangiopericytoma, spastic diseases of the urinary tract and/or bladder, hepatorenal syndrome, immunological diseases involving vasculitis such as lupus, systemic sclerosis, mixed cryoglobulinemia, fibrosis associated with renal dysfunction and hepatotoxicity;
- for use in gastrointestinal diseases such as ulcerative colitis, Crohn's disease, gastric mucosal damage, ulcer inflammatory bowel disease and ischemic bowel disease, gall bladder or bile duct-based diseases such as cholangitis, pancreatitis, regulation of cell growth, beginning prostatic hypertrophy, or transplantation, or for use as anti-diarrheal agent;
- for the treatment of disorders involving bronchoconstriction or disorders of chronic or acute inflammation such as obstructive pulmonary disease and adult distress syndrome;
- for the alleviation of pain including neuropathic pain, peripheral pain and pain associated with cancer such as pain associated with prostate cancer or bone-cancer;
- for the treatment of central nervous system vascular disorders such as stroke, transient ischemic attacks, migraine and subarachnoid hemorrhage, central nervous system behavioural disorders, treatment of dementia including Alzheimer's dementia, senile dementia and vascular dementia, epilepsy, or sleep disorders; or
- for reduction of general morbidity and/or mortality as a result of above utilities.

The present invention also relates to a method for the prevention or treatment of a disease or disorder mentioned herein comprising administering to a subject a pharmaceutically active amount of a crystalline salt, especially of an essentially pure crystalline salt, of COMPOUND according to any one of embodiments 1) to 51).

Furthermore, the crystalline salts, especially the essentially pure crystalline salts, of COMPOUND according to any one of embodiments 1) to 51) may also be used favourably in combination with one or more agents selected from lipid lowering agents such as statins, anticoagulants such as coumarins, antithrombotic agents such as clopidogrel, β-blockers, and other cardioprotective agents.

The present invention also relates to a process for the preparation of COMPOUND in racemic and enantiomerically enriched form, and to processes for the preparation and characterization of crystalline salts of COMPOUND according to any one of embodiments 1) to 51), said processes are described in the experimental part below.

EXPERIMENTAL PART

The following Examples illustrate the invention in more detail. Temperatures are given in degrees Celsius. If not stated otherwise percentages are given by weight.

| Abbreviations as used herein and in the description above: | |
|---|---|
| aq. | aqueous |
| ca. | about |
| CC | column chromatography on silica gel |
| DCM | dichloromethane |
| DIPA | diisopropyl-amine |
| DIPEA | diisopropyl-ethylamine, Hünig's base, ethyl-diisopropylamineDMAP 4-dimethylamino-pyridine |
| DMF | dimethylformamide |
| DSC | differential scanning calorimetry |
| eq. | equivalent(s) |
| Et$_2$O | diethyl ether |
| EtOAc | ethyl acetate |
| EtOH | ethanol |
| FIG. | figure |
| h | hour(s) |
| $^1$H-NMR | hydrogen-1 nuclear magnetic resonance |
| Hept | heptane |
| Hex | hexane |
| HOBt | 1-hydroxybenzotriazole |
| MEK | 2-butanone |
| MeCN | acetonitrile |
| MeOH | methanol |
| NEt$_3$ | triethylamine |

-continued

| Abbreviations as used herein and in the description above: | |
|---|---|
| Pd/C | palladium on carbon |
| 2-PrOH | isopropanol |
| Red-Al | sodium-bis(2-methoxyethoxy)aluminumhydride |
| RH | relative humidity |
| rt | room temperature |
| rpm | rotations per minute |
| sat. | saturated |
| TBME | tert-butyl methyl ether |
| tert. | tertiary |
| THF | tetrahydrofuran |
| TsOH | para (p)-toluene sulfonic acid |
| XRPD | X-ray powder diffraction |

X-ray Powder Diffraction Analysis (XRPD):

Method 1: X-ray powder diffraction patterns were collected on a Bruker D8 Advance X-ray diffractometer equipped with a LynxEye detector with 3° window operated with Cu Kα-radiation in reflection geometry (Bragg-Brentano). Typically, the X-ray tube was run at 40 kV/40 mA. A step size of 0.02° (2θ) and a step time of 37 sec over a scanning range of 2-50° in 2theta (2θ) were applied. The divergence slit was set to variable V12 or V20, dependent on sample holder depth. The powder (about 15 mg for 0.1 mm depth and about 80 mg for 1 mm depth) was slightly pressed into a silicon single crystal sample holder with depth of 0.1 mm or 1 mm and samples were rotated in their own plane during the measurement. Selected samples were covered with Kapton foil. Diffraction data are reported using Cu Kα1 (λ=1.5406 Å), after the Kα2 component has been stripped using the instrument evaluation software (EVA). In addition, the background signal has been removed using the instrument evaluation software (EVA), for samples that were covered by Kapton during data acquisition. The accuracy of the 2θ values as provided herein is in the range of +/−0.1-0.2° as it is generally the case for conventionally recorded X-ray powder diffraction patterns.

Method 2: X-ray powder diffraction patterns were collected on a Bruker D8 HTS X-ray diffractometer equipped with a GADDS HiStar detector operated with Cu Kα-radiation in reflection geometry. Typically, the X-ray tube was run at 40 kV/40 mA. The instrument is performance checked using a certified Corundum standard (NIST 1976). Samples run under ambient conditions were prepared as flat plate specimens using powder as received. Approximately 3 mg of the sample was gently pressed on a microscopy slide. The data were collected over an angular range of 7.6° to 26.7° 2θ in 1 frame with an acquisition time of 180 second. Diffraction data are reported without Kα2 component stripping and the background signal has been removed using the instrument evaluation software (EVA). The accuracy of the 2θ values as provided herein is in the range of +/−0.1-0.2° as it is generally the case for conventionally recorded X-ray powder diffraction patterns.

Melting points were measured on a Buchi B-540 apparatus and are not corrected; or were measured, if explicitly stated, by differential scanning calorimetry (DSC):

DSC data were collected on a Perkin Elmer DSC7. Typically 2-3 mg of sample, previously stored open under dry nitrogen for 16 hours, were heated in a closed gold pan at 20° C. min$^{-1}$ from −20° C. to 200° C. Melting points are reported as peak temperatures.

Optical rotations were measured on a Jasco P-1030 apparatus at room temperature using the D-line of sodium (λ=589 nm).

$^1$H-NMR were measured on a Bruker Avance 400 (400 MHz); chemical shifts are given in ppm relative to the solvent used; multiplicities: s=singlet, d=doublet, t=triplet, q=quartet, p=pentuplet, hex=hexet, sept=septuplet, m=multiplet, dm=doublet of multiplet, br=broad, coupling constants are given in Hz). NMR assays were measured using hydroquinone dimethylether as internal standard.

Hygroscopicity was assessed through scanned gravimetric vapour sorption measurements on a SPS11-100m (Projekt Messtechnik, Ulm, Germany) (scan rate was 5% relative humidity change per hour, cycle started at 50% relative humidity followed by a scan to dryness and an upwards scan to 95% relative humidity). Classification was done according to the European Pharmacopea Technical Guide (1999 edition) (e.g. slightly hygroscopic: increase in mass is less than 2% and equal to or greater than 0.2% mass/mass). The mass change between 40% relative humidity and 80% relative humidity in the upwards scan was considered.

LC-MS were run using the following conditions: Finnigan Navigator with HP 1100 Binary Pump and DAD, column: 4.6×50 mm, Zorbax SB-AQ, 5 μm, 120 Å, gradient: 5-95% acetonitrile in water, 1 min, with 0.04% trifluoroacetic acid, flow: 4.5 mL/min, $t_R$ is given in min.

Compounds are purified by preparative HPLC (column: X-terra RP18, 50×19 mm, 5 μm, gradient: 10-95% acetonitrile in water containing 0.5% (of formic acid) or by column chromatography on silica gel. Racemates can be separated into their enantiomers by preparative HPLC (preferred conditions: Daicel, ChiralCel OD 20×250 mm, 10 μm, 4% ethanol in hexane, flow 10-20 mL/min).

I. Preparation and Characterization of COMPOUND

The preparation of COMPOUND is known from WO2008/132679:

Preparation of Intermediates

General Procedures for the Preparation of Key Intermediates K:

Key intermediates K1A and K2A which are bicyclo[2.2.2]oct-5-en-2-yl or bicyclo[3.2.2]non-8en-6-yl derivatives are obtained as a mixture between the major racemate having the relative configuration (R*,R*,R*) (i.e. the bridge —(CH$_2$)$_2$— of the cyclohexene moiety is cis to the group —OR$^2$ being hydroxy) and the minor racemate having the relative configuration (R*,S*,R*) (i.e. the bridge —(CH$_2$)$_2$— of the cyclohexene moiety is trans to the group —OR$^2$ being hydroxy). The major and the minor racemates can be separated as described for key intermediate K1A in procedure A1.5. The major racemate is isolated and used in the preparation of the examples below.

K1A: rac-(1R*,2R*,4R*)-(2-Hydroxy-5-phenyl-bicyclo[2.2.2]oct-5-en-2-yl)-acetic acid tert.-butyl ester K1 A.1 (Procedure A1.1):
rac-(1R*,4R*)-Bicyclo[2.2.2]octane-2,5-dione 25 mL of 2-(trimethylsilyloxy)-1,3-cyclohexadiene and 13 mL of α-acetoxyacrylonitrile were mixed and heated at 150° C. in a closed vessel for 22 h. The obtained dark orange viscous oil was dissolved in 200 mL of MeOH. After dropwise addition of a solution of 2.2 g of sodium methoxide in 150 mL of MeOH the reaction mixture was stirred for 3 h at rt, poured into ice/water and extracted with DCM. The organic phases were concentrated in vacuo and the crude residue was purified by CC with EtOAc-Hept (1:2) to yield 7.9 g of rac-(1R*,4R*)-bicyclo[2.2.2]octane-2,5-dione.

LC-MS: $t_R$=0.44 min.

K1A.2 (Procedure A1.2): rac-(1R*,4R*)-Spiro[bicyclo[2.2.2]octane-2,2'-[1,3]dioxolan]-5-one To 4.0 g of rac-(1R*,4R*)-bicyclo[2.2.2]octane-2,5-dione (intermediate K1A.1), dissolved in 120 mL of toluene, 1.7 mL of ethylene glycol and 0.27 g of TsOH were added and the solution was heated under vigorous stirring to reflux for 3.5 h. The reaction mixture was cooled to rt, quenched with saturated aq. NaHCO$_3$, extracted with Et$_2$O, and the organic phase was evaporated. The crude product was purified by CC with Hex-EtOAc (7:3) to yield 2.41 g of rac-(1R*,4R*)-spiro[bicyclo[2.2.2]octane-2,2'-[1,3]dioxolan]-5-one as yellow oil.

LC-MS: $t_R$=0.64 min; [M+H+CH$_3$CN]$^+$: 224.35.

K1A.3 (Procedure A1.3): Mixture of rac-(7R*,8R*,10R*)- and rac-(7R*,8S*,10R*)-7,10-(1,2-Ethylen)-8-phenyl-1,4-dioxa-spiro[4.5]decan-8-ol To a solution of 2.41 g of rac-(1R*,4R*)-spiro[bicyclo[2.2.2]octane-2,2'-[1,3]dioxolan]-5-one (intermediate K1A.2) in 80 mL Et$_2$O, 14.5 mL phenylmagnesium bromide solution (1M in Et$_2$O) was added dropwise over 10 min. The reaction mixture was stirred for 4 h at rt. Then, the mixture was quenched carefully with ice, 8 mL 2N HCl were added and the phases were separated. The organic phase was evaporated and the crude product was purified by CC with Hept-EtOAC (7:3) to give 0.37 g of 7,10-(1,2-ethylen)-8-phenyl-1,4-dioxa-spiro[4.5]decan-8-ol as colorless oil. (Separation of the diastereomers by CC is possible but was not performed here.)

LC-MS: $t_R$=0.84 min; [M−H$_2$O+H]$^+$: 243.34.

K1A.4 (Procedure A1.4): rac-(1R*,4R*)-5-Phenyl-bicyclo[2.2.2]oct-5-en-2-one

To a solution of 0.54 g of 7,10-(1,2-ethylen)-8-phenyl-1,4-dioxa-spiro[4.5]decan-8-ol (intermediate K1A.3) in 20 mL acetone was added 200 mg of TsOH and then the mixture was stirred for 2 d at rt. The reaction mixture was quenched with sat. aq. NaHCO$_3$, extracted with EtOAC and the organic phase was evaporated. The crude product was purified by CC with Hept-EtOAC (7:3) to give 0.34 g of rac-(1R*,4R*)-5-phenyl-bicyclo[2.2.2]oct-5-en-2-one as colorless oil.

LC-MS: $t_R$=0.93 min; [M+H+CH$_3$CN]$^+$: 240.11.

K1A.5 (Procedure A1.5): rac-(1R*,2R*,4R*)-(2-Hydroxy-5-phenyl-bicyclo[2.2.2]oct-5-en-2-yl)-acetic acid tert.-butyl ester and rac-(1R*,2S*,4R*)-(2-hydroxy-5-phenyl-bicyclo[2.2.2]oct-5-en-2-yl)-acetic acid tert.-butyl ester To a solution of 0.51 mL of DIPA in 0.5 mL THF 2.2 mL of n-butyllithium (1.6M in Hex) were added dropwise at −20° C. After 10 min, 0.5 mL of toluene were added and the solution was stirred for 30 min. The mixture was cooled to −50° C., 0.73 mL of tert.-butyl acetate were added and stirring was continued for 1 h at −50° C. Then 0.32 g of rac-(1R*,4R*)-5-phenyl-bicyclo[2.2.2]oct-5-en-2-one (intermediate K1A.4) dissolved in 1 mL of THF was added and the solution was stirred at −50 to −20° C. over 2.5 h. The reaction mixture was poured on ice/aq. HCl, the organic phase was separated, washed and evaporated. The crude reaction product was purified by CC with Hept-EtOAc (9:1) to yield 0.30 g of the major racemate, rac-(1R*,2R*,4R*)-2-hydroxy-5-phenyl-bicyclo[2.2.2]oct-5-en-2-yl)-acetic acid tert.-butyl ester, as white solid and 0.07 g of the minor racemate, rac-(1R*,2S*,4R*)-2-hydroxy-5-phenyl-bicyclo[2.2.2]oct-5-en-2-yl)-acetic acid tert.-butyl ester, as colorless oil.

LC-MS (major racemate): $t_R$=1.06 min; [M−(CH$_3$)$_3$−H$_2$O+H]$^+$: 241.11.

LC-MS (minor racemate): $t_R$=1.05 min; [M+H]$^+$: 315.18.

K1A.6: (1S,2S,4S)-(2-Hydroxy-5-phenyl-bicyclo[2.2.2]oct-5-en-2-yl)-acetic acid tert.-butyl ester and (1R,2R,4R)-(2-Hydroxy-5-phenyl-bicyclo[2.2.2]oct-5-en-2-yl)-acetic acid tert.-butyl ester rac-(1R*,2R*,4R*)-(2-Hydroxy-5-phenyl-bicyclo[2.2.2]oct-5-en-2-yl)-acetic acid tert.-butyl ester was separated into the respective enantiomers using prep. chiral HPLC (column: Daicel ChiralPak AD-H, 20×250 mm, 5 μm; Hex/EtOH 95:5, flow 16 mL/min)

Chiral analytic HPLC (Daicel ChiralPak AD-H, 4.6×250 mm, 5 μm; Hex/EtOH 95:5, flow 0.8 mL/min):

(1R,2R,4R)-(2-Hydroxy-5-phenyl-bicyclo[2.2.2]oct-5-en-2-yl)-acetic acid tert.-butyl ester:
Enantiomer A: $t_R$=7.93 min.
(1S,2S,4S)-(2-Hydroxy-5-phenyl-bicyclo[2.2.2]oct-5-en-2-yl)-acetic acid tert.-butyl ester:
Enantiomer B: $t_R$=7.93 min.

BB. [3-(4,7-Dimethoxy-1H-benzoimidazol-2-yl)-propyl]-methyl-amine

BB.1 3,6-Dimethoxy-benzene-1,2-diamine 3,6-Dimethoxy-benzene-1,2-diamine was synthesized by dissolving 6.0 g of 1,4-dimethoxy-2,3-dinitro-benzene (Eur. J. Org. Chem. 2006, 2786-2794) in 220 mL EtOH, evacuating 3 times with N$_2$ and adding 600 mg of 10 wt % Pd/C. The reaction was stirred under a H$_2$ atmosphere (balloon). Another 300 mg of 10 wt % Pd/C were added after 2 days and the mixture was stirred for another 24 h. Filtration over a pad of celite and washing with EtOH and EtOAc yielded after concentration in vacuo 4.3 g of 3,6-dimethoxy-benzene-1,2-diamine as black solid.

LC-MS: $t_R$=0.48 min; [M+H]$^+$: 169.09.

BB.2 [3-(2-Amino-3,6-dimethoxy-phenylcarbamoyl)-propyl]-methyl-carbamic acid benzyl ester To a solution of 3.1 g of 4-(benzyloxycarbonyl-methyl-amino)-butyric acid in 80 mL DCM were added 6.5 mL of DIPEA, 1.8 g of HOBt, 2.6 g of EDC and 154 mg of DMAP. After stirring for 10 min, 2.1 g of 3,6-dimethoxy-benzene-1,2-diamine, dissolved in 20 mL DCM, were added and the mixture was stirred at rt overnight. The reaction was quenched with sat. aq. NaHCO$_3$, the phases were separated and the organic phase was washed with brine, dried over MgSO$_4$ and concentrated in vacuo to yield the crude title compound as black oil.

LC-MS: $t_R$=0.88 min; [M+H]$^+$: 402.06.

BB.3 [3-(4,7-Dimethoxy-1H-benzoimidazol-2-yl)-propyl]-methyl-carbamic acid benzyl ester To a mixture of the above crude 3-(2-amino-3,6-dimethoxy-phenylcarbamoyl)-propyl]-methyl-carbamic acid benzyl ester in 16 mL toluene were added 4 mL of DMF and 1.9 g of TsOH and the reaction was heated to 150° C. for 2 h in the microwave. Sat. aq. NaHCO$_3$ was added and the phases were separated. The organic phase was washed with brine, dried over MgSO$_4$, concentrated in vacuo, filtered over a short pad of silica gel with EtOAc and concentrated again. Purification by CC with EtOAc yielded 2.7 g of 3-(4,7-dimethoxy-1H-benzoimidazol-2-yl)-propyl]-methyl-carbamic acid benzyl ester as brown resin.

LC-MS: $t_R$=0.85 min; [M+H]$^+$: 384.62.

BB.4 [3-(4,7-Dimethoxy-1H-benzoimidazol-2-yl)-propyl]-methyl-amine

A solution of 2.6 g of 3-(4,7-dimethoxy-1 H-benzoimidazol-2-yl)-propyl]-methyl-carbamic acid benzyl ester in 60 mL EtOH was evacuated 3 times with N$_2$ before 260 mg of 10 wt % Pd/C were added. The reaction mixture was then stirred under a H$_2$ atmosphere (balloon) for 5 h at rt. Filtration over a pad of celite and washing with EtOH yielded after concentration in vacuo 1.7 g of 3-(4,7-dimethoxy-1H-benzoimidazol-2-yl)-propyl]-methyl-amine as brown foam.

LC-MS: $t_R$=0.57 min; [M+H]$^+$: 250.13.

Preparation of COMPOUND

Reference Example 1A rac-Isobutyric acid (1R*,2R*,4R*)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester 1.1 (Procedure P1.1): rac-(1R*,2R*,4R*)-(2-Hydroxy-5-phenyl-bicyclo[2.2.2]oct-5-en-2-yl)-acetic acid To a solution of 4.0 g of rac-(1R*,2R*,4R*)-(2-hydroxy-5-phenyl-bicyclo[2.2.2]oct-5-en-2-yl)-acetic acid tert.-butyl ester in 25 mL EtOH were added 2.1 g of LiOH.H$_2$O, 8 mL H$_2$O and 22 mL MeOH. The reaction mixture was stirred at rt for 3 d and then concentrated. The residue was partitioned between water and Et$_2$O. The aq. layer was separated and acidified with 1N HCl resulting in the formation of a white solid. The solid was filtrated, washed with 5 mL aq. HCl and dried in vacuo to obtain 3.2 g of rac-(1R*,2R*,4R*)-(2-hydroxy-5-phenyl-bicyclo[2.2.2]oct-5-en-2-yl)-acetic acid as white solid.

LC-MS: $t_R$=0.86 min; [M−H$_2$O+H]$^+$: 241.28.

1.2 (Procedure P1.2): rac-(1R*,2R*,4R*)-N-[3-(4,7-Dimethoxy-1H-benzoimidazol-2-yl)-propyl]-2-(2-hydroxy-5-phenyl-bicyclo[2.2.2]oct-5-en-2-yl)-N-methyl-acetamide To a solution of 280 mg of rac-(1R*,2R*,4R*)-(2-hydroxy-5-phenyl-bicyclo[2.2.2]oct-5-en-2-yl)-acetic acid in 7 mL THF were added 0.58 mL of DIPEA, 175 mg of HOBt and 250 mg of EDC at rt. After stirring for 10 min, 270 mg of 3-(4,7-dimethoxy-1H-benzoimidazol-2-yl)-propyl]-methyl-amine were added and the reaction mixture was stirred at rt overnight. The reaction mixture was quenched with sat. aq. NaHCO$_3$, the phases were separated and the organic phase was washed with water and brine, dried over MgSO$_4$ and concentrated in vacuo. Purification by CC using EtOAc-MeOH (5:1 to 2:1) yielded 475 mg of rac-(1R*,2R*,4R*)-N-[3-(4,7-dimethoxy-1H-benzoimidazol-2-yl)-propyl]-2-(2-hydroxy-5-phenyl-bicyclo[2.2.2]oct-5-en-2-yl)-N-methyl-acetamide as white foam.

LC-MS: $t_R$=0.91 min; [M+H]$^+$: 490.06.

1.3 (Procedure P1.3): rac-(1R*,2R*,4R*)-2-(2-{[3-(4,7-Dimethoxy-1H-benzoimidazol-2-yl)-propyl]-methyl-amino}-ethyl)-5-phenyl-bicyclo[2.2.2]oct-5-en-2-ol To a solution of 310 mg of rac-(1R*,2R*,4R*)-N-[3-(4,7-dimethoxy-1H-benzoimidazol-2-yl)-propyl]-2-(2-hydroxy-5-phenyl-bicyclo[2.2.2]oct-5-en-2-yl)-N-methyl-acetamide in 8 mL toluene were added dropwise 0.77 mL of a Red-Al solution (65% in toluene) at 0° C. After stirring for 10 min at 0° C., the cooling bath was removed and stirring was continued for 3 h at rt. The reaction mixture was then carefully poured onto a mixture of 1M NaOH/ice and stirred for 10 min. The aq. phase was extracted with toluene, the combined organic phases were washed with brine, dried over MgSO$_4$ and concentrated in vacuo. Purification by CC using EtOAc-MeOH (2:1) yielded 230 mg of rac-(1R*,2R*,4R*)-2-(2-{[3-(4,7-dimethoxy-1H-benzoimidazol-2-yl)-propyl]-methyl-amino}-ethyl)-5-phenyl-bicyclo[2.2.2]oct-5-en-2-ol as white foam.

LC-MS: $t_R$=0.79 min; [M+H]$^+$: 476.13.

1.4: rac-Isobutyric acid (1R*,2R*,4R*)-2-(2-{[3-(4, 7-dimethoxy-1H-benzoimidazol-2-yl)-propyl]-methyl-amino}-ethyl)-5-phenyl-bicyclo[2.2.2]oct-5-en-2-yl ester To a solution of 199 mg of rac-(1R*,2R*,4R*)-2-(2-{[3-(4,7-dimethoxy-1H-benzoimidazol-2-yl)-propyl]-methyl-amino}-ethyl)-5-phenyl-bicyclo[2.2.2]oct-5-en-2-ol in 4 mL DCM were added 0.2 mL of NEt$_3$ and 0.1 mL of isobutyryl-chloride at 0° C. The reaction mixture was stirred overnight allowing the temperature to reach slowly rt. The reaction was quenched with sat. aq. NaHCO$_3$, the phases were separated and the water phase was re-extracted with DCM. The combined organic phases were washed with brine, dried over MgSO$_4$ and concentrated in vacuo. The residue was redissolved in 3 mL EtOAc, silica gel and 1.5 mL MeOH were added and the mixture was stirred vigorously for 7 d. The mixture was filtered, thouroughly washed with EtOAc-MeOH (2:1) and evaporated. Purification by CC using EtOAc-MeOH (5:1 to 3:1+0.1% NEt$_3$) yielded 186 mg of rac-isobutyric acid (1R*,2R*,4R*)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester as beige foam.

LC-MS: $t_R$=0.90 min; [M+H]$^+$: 546.23.

Reference Example 2A

Isobutyric acid (1S,2S,4S)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester 2.1: (1S,2S,4S)-(2-Hydroxy-5-phenyl-bicyclo[2.2.2] oct-5-en-2-yl)-acetic acid Prepared according to procedure P1.1 in Reference Example 1A using enantiomer B of rac-(1R*,2R*,4R*)-(2-hydroxy-5-phenyl-bicyclo[2.2.2]oct-5-en-2-yl)-acetic acid tert.-butyl ester (see K1A.6).

LC-MS: $t_R$=0.91 min; [M−H$_2$O+H]$^+$: 241.10.

2.2: (1S,2S,4S)-2-(2-{[3-(4,7-Dimethoxy-1H-benzoimidazol-2-yl)-propyl]-methyl-amino}-ethyl)-5-phenyl-bicyclo[2.2.2]oct-5-en-2-ol Prepared according to procedures P1.2 to P1.3 in Reference Example 1A using the above (2-hydroxy-5-phenyl-bicyclo[2.2.2]oct-5-en-2-yl)acetic acid.

LC-MS: $t_R$=0.78 min; [M+H]$^+$: 476.09.

2.3: Isobutyric acid (1S,2S,4S)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester Prepared according to procedure P1.4 in Reference Example 1A using the above 2-(2-{[3-(4,7-dimethoxy-1H-benzoimidazol-2-yl)-propyl]-methyl-amino}-ethyl)-5-phenyl-bicyclo[2.2.2]oct-5-en-2-ol.

LC-MS: $t_R$=0.89 min; [M+H]$^+$: 546.19.

Reference Example 3A

Isobutyric acid (1R,2R,4R)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester

3.1: (1R,2R,4R)-(2-Hydroxy-5-phenyl-bicyclo[2.2.2]oct-5-en-2-yl)-acetic acid Prepared according to procedure P1.1 in Reference Example 1 using enantiomer A of rac-(1R*,2R*,4R*)-(2-hydroxy-5-phenyl-bicyclo[2.2.2]oct-5-en-2-yl)-acetic acid tert.-butyl ester (see K1A.6).

LC-MS: $t_R$=0.91 min; [M−H$_2$O+H]$^+$: 241.16.

3.2: (1R,2R,4R)-2-(2-{[3-(4,7-Dimethoxy-1H-benzoimidazol-2-yl)-propyl]-methyl-amino}-ethyl)-5-phenyl-bicyclo[2.2.2]oct-5-en-2-ol Prepared according to procedures P1.2 to P1.3 in Reference Example 1 using the above (2-hydroxy-5-phenyl-bicyclo[2.2.2]oct-5-en-2-yl)-acetic acid.

LC-MS: $t_R$=0.79 min; [M+H]$^+$: 476.09.

3.3: Isobutyric acid (1R,2R,4R)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester Prepared according to procedure P1.4 in Reference Example 1A using the above 2-(2-{[3-(4,7-dimethoxy-1H-benzoimidazol-2-yl)-propyl]-methyl-amino}-ethyl)-5-phenyl-bicyclo[2.2.2]oct-5-en-2-ol.

LC-MS: $t_R$=0.89 min; [M+H]$^+$: 546.11.

Optical rotation: alpha D (c=10 mg/mL EtOH)=−21.5°.

1H NMR (MeOD, 400 MHz) δ7.39-7.37 (m, 2H), 7.30 (t, J=6.4 Hz, 2H), 7.24-7.20 (m, 1H), 6.60 (s, 2 H), 6.43 (br d, J=7.6 Hz, 1H), 3.91 (s, 6H), 3.27-3.23 (m, 1H), 3.18-3.15 (m, 1H), 2.87 (t, J=7.6 Hz, 2H), 2.54 (sept, J=7.0 Hz, 1H), 2.47-2.37 (m, 4H), 2.21 (s, 3H), 2.19-2.12 (m, 1H), 2.01-1.92 (m, 5H), 1.75-1.65 (m, 2H), 1.48-1.38 (m, 1H), 1.27-1.19 (m, 1H), 1.16 (d, J=7.0 Hz, 6H).

Biological Tests

In vitro Assay L Channel

The L channel antagonistic activity (IC$_{50}$ values) of Reference Examples 1A, 2A, and 3A is determined in accordance with the following experimental method.

Human embryonic kidney (HEK293) cells expressing the human Ca$_v$1.2 channel in addition to the auxiliary subunits β-2a and α2δ-1, are grown in culture medium (DMEM containing 10% heat-inactivated fetal calf serum (FCS), 100 U/ml penicillin, 100 µg/ml streptomycin, 100 µg/ml G418, 40 µg/ml zeocin and 100 µg/ml hygromycin). The cells are seeded at 20.000 cells/well into 384-well black clear bottom sterile plates (poly-L-lysine-coated, Becton Dickinson). The seeded plates are incubated overnight at 37° C. in 5% CO$_2$. The KCl solution is prepared as 80 mM stock solution in assay buffer (HBSS containing 0.1% BSA, 20 mM HEPES, 0.375 g/l NaHCO$_3$, adjusted to pH 7.4 with NaOH) for use in the assay at a final concentration of 20 mM. Antagonists are prepared as 10 mM stock solutions in DMSO, then diluted in 384 w plates first in DMSO, then in assay buffer to obtain 3× stocks. On the day of the assay, 25 µl of staining buffer (HBSS containing 20 mM HEPES, 0.375 g/l NaHCO$_3$, and 3 µM of the fluorescent calcium indicator fluo-4 AM (1 mM stock solution in DMSO, containing 10% pluronic) is added to each well of the seeded plate. The 384-well cell-plates are incubated for 60 min at 37° C. in 5% CO$_2$ followed by washing with 2×50 µl per well using assay buffer leaving 50 µl/well of this buffer for equilibration at room temperature (30-60 min). Within the Fluorescent Imaging Plate Reader (FLIPR, Molecular Devices), antagonists are added to the plate in a volume of 25 µl/well, incubated for 3 min and finally 25 µl/well of KCl solution is added for cellular depolarization. Fluorescence is measured for each well at 2 second intervals for 8 minutes, and the area under the curve of each fluorescence peak is compared to the area of the fluorescence peak induced by 20 mM KCl with vehicle in place of antagonist. For each antagonist, the IC$_{50}$ value (the concentration (in nM) of compound needed to inhibit 50% of the KCl-induced fluorescence response) up to 10 µM is determined.

IC$_{50}$ values of reference example compounds 1A, 2A, and 3A have been measured and are in the range of 156 to 439 nM.

In vitro Assay T Channel:

The T channel antagonistic activity (IC$_{50}$ values) of Reference Examples 1A, 2A, and 3A is determined in accordance with the following experimental method and data are shown in Table 1.

Human embryonic kidney (HEK293) cells expressing the human Ca$_v$3.1 Ca$_v$3.2 or Ca$_v$3.3 channel, respectively, are grown in culture medium (DMEM containing 10% heat-inactivated fetal calf serum (FCS), 100 U/ml penicillin, 100 µg/ml streptomycin and 1 mg/ml G418). The cells are seeded at 20.000 cells/well into 384-well black clear bottom sterile plates (poly-L-lysine-coated, Becton Dickinson). The seeded plates are incubated overnight at 37° C. in 5% CO$_2$. The Ca$^{2+}$ solution is prepared as 100 mM stock solution in 100 mM tetraethylammoniumchloride (TEA-chloride), 50 mM HEPES, 2.5 mM CaCl$_2$, 5 mM KCl, 1 mM MgCl$_2$, adjusted to pH 7.2 with TEA-hydroxide, for use in the assay at a final concentration of 10 mM. Antagonists are prepared as 10 mM stock solutions in DMSO, then diluted in 384 w plates first in DMSO, then in 100 mM TEA-chloride, 50 mM HEPES, 2.5 mM CaCl$_2$, 5 mM KCl, 1 mM MgCl$_2$, adjusted to pH 7.2 with TEA-hydroxide, to obtain 9× stocks. On the day of the assay, 25 µl of staining buffer (HBSS containing 20 mM HEPES, 0.375 g/l NaHCO$_3$ and 3 µM of the fluorescent calcium indicator fluo-4 AM (1 mM stock solution in DMSO, containing 10% pluronic) is added to each well of the seeded plate. The 384-well cell-plates are incubated for 60 min at 37° C. in 5% $CO_2$ followed by washing with 2×50 µl per well using HBSS containing 0.1% BSA, 20 mM HEPES, 0.375 g/l $NaHCO_3$, leaving 50 µl/well of this buffer for equilibration at room temperature (30-60 min). Within the Fluorescent Imaging Plate Reader (FLIPR, Molecular Devices), antagonists are added to the plate in a volume of 6.25 µl/well, incubated for 3 min, and finally 6.25 µl/well of $Ca^{2+}$ solution is added. Fluorescence is measured for each well at 2 second intervals for 8 minutes, and the area under the curve of each fluorescence peak is compared to the area of the fluorescence peak induced by 10 mM $Ca^{2+}$ with vehicle in place of antagonist. For each antagonist, the $IC_{50}$ value (the concentration (in nM) of compound needed to inhibit 50% of the $Ca^{2+}$-induced fluorescence response) up to 10 µM is determined.

TABLE 1

| Compound of reference example | $IC_{50}$ |
|---|---|
| 2A | 778 |
| 3A | 793 |

Effect on Isolated Hearts According to the Langendorff Method (Lgdff)

The Reference Examples 1A, 2A, and 3A were tested for their potential to reduce blood pressure and their effect on the contractility of the heart muscle. $EC_{50}$ values on isolated mouse hearts were determined according to Literature (Doring H J., The isolated perfused heart according to Langendorff technique—function—application, Physiol. Bohemoslov. 1990, 39(6), 481-504; Kligfield P, Homer H, Brachfeld N., A model of graded ischemia in the isolated perfused rat heart, J. Appl. Physiol. 1976 June, 40(6), 1004-8).

The compound of reference example 1A has been measured using the procedure described above for the Langendorff experiment with an $EC_{50}$ of 5 nM.

II. Preparation of Salt Forms of COMPOUND

II.a) General Procedure for Salt Formation with COMPOUND:

1 eq. of COMPOUND was dissolved in SOLVENT1. The solution was brought to 50° C. 2 Equivalents of acid dissolved in SOLVENT2 was added. The mixture was stirred at 50° C. for 5 min and the heating source was turned off. The mixture was allowed to cool to rt within 1 hour. If a precipitate was observed the mixture was filtered and the solid was isolated. In case that no solid was obtained the mixture was evaporated to dryness and 6 volumes of heptane were added. The mixture was heated to reflux, 3 volumes of EtOAc were added until all dissolved. In case that dissolution was not complete further 3 volumes EtOAc were added. If dissolution was still not complete, as less as possible MeOH was added until complete dissolution. The mixture was allowed to cool slowly to rt. At rt the vessel was scratched with a spatula and was further cooled to 0° C. The mixture was filtered and the solution was evaporated to dryness on the rotavapor.

The term "volumes" as used herein signifies 1 L for 1 kg of solid material.

SOLVENT1=8 volumes EtOAc for: benzensulfonic acid, benzoic acid, salicylic acid, saccharin, para-toluenesulfonic acid, malonic acid, methanesulfonic acid, naphthalene-2-sulfonic acid, naphthalene-1,5-disulfonic acid, ethanesulfonic acid, malic acid, glycolic acid, ketoglutaric acid, and fumaric acid;

SOLVENT1=1.8 volumes EtOAc for: hydrobromic acid, and hydrochloric acid;

SOLVENT1=8 volumes acetone for: sulfuric acid, and phosphoric acid;

SOLVENT1=7 volumes acetone for: citric acid, succinic acid, and tartaric acid.

SOLVENT2=7 volumes EtOAc for: citric acid;

SOLVENT2=3 volumes EtOAc for: benzensulfonic acid, benzoic acid, methanesulfonic acid, salicylic acid, and saccharin (partially soluble);

SOLVENT2=3 volumes MeOH for: para-toluenesulfonic acid, malonic acid, naphthalene-2-sulfonic acid, naphthalene-1,5-disulfonic acid, malic acid, glycolic acid, ketoglutaric acid, and fumaric acid;

SOLVENT2=15 volumes acetone for: succinic acid;

SOLVENT2=12 volumes EtOH for: tartaric acid;

SOLVENT2=water for: hydrobromic acid, hydrochloric acid, sulfuric acid, and phosphoric acid.

Results obtained using the general procedure described above are summarized in Tables 1 and 2. In case particular procedures have been used to prepare crystalline salt forms of COMPOUND, such procedures are described in Reference Example S1 and the Examples S2 to S7 below.

TABLE 1

Characterisation data for crystalline salt forms of COMPOUND gained according to the general procedure

| Salt | Melting point/1H-NMR | XRPD |
|---|---|---|
| di-hydrobromic acid salt | Melting point at about 93° C. 1H-NMR consistent with structure. The X-ray diffraction diagram measured with method 2 shows peaks having a relative intensity, as compared to the most intense peak in the diagram, of the following percentages (relative peak intensitites given in parenthesis) at the indicated angles of refraction 2theta (selected peaks from the range 8-26.5° 2theta with relative intensity larger then 10% are reported): 9.1° (22%), 9.5° (62%), 12.3° (23%), 12.6° (27%), 14.1° (36%), 14.6° (18%), 15.3° (86%), 15.8° (49%), 17.0° (71%), 17.9° (100%), 19.1° (81%), 19.6° (67%), 20.2° (52%), 20.6° (44%), 21.1° (54%), 22.5° (35%), 23.6° (16%), 24.5° (48%), 25.0° (42%), 25.4° (28%), and 26.1° (43%). The above peaks correspond to FIG. 7 measured for Example S7 below. A shift of 2theta of | Crystalline, crystalline form identical to Example S7 below |

TABLE 1-continued

Characterisation data for crystalline salt forms of COMPOUND
gained according to the general procedure

| Salt | Melting point/1H-NMR | XRPD |
|---|---|---|
| sesqui-naphthalene-1,5-disulfonic acid salt | 0.2-0.3° may be explained by the use of method 1 for the measurement of the X-ray diffraction diagram in Example S7.<br>1H-NMR (D6-DMSO, 400 MHz, only main peaks described) δ 8.88 (d, J = 9.2 Hz, 2.7 H, 1.5 molecules of naphthalene-1,5-disulfonic acid), 7.94 (d, J = 7.0 Hz, 2.7 H, 1.5 molecules of naphthalene-1,5-disulfonic acid), 7.47-7.25 (m, 8.6 H, 1.5 molecules of naphthalene-1,5-disulfonic acid + 5H), 6.99 (s, 2H), 6.54 (dd, J = 8.0 Hz, 1H), 3.94 (s, 6H), 3.24-3.03 (m, 8H), 2.72 (s, 3H), 2.56 (sept, J = 7.0 Hz, 1H), 1.14-1.06 (m, 6H). | Crystalline, see FIG. 8 |
| di-benzensulfonic acid salt | 1H-NMR (MeOD, 400 MHz) δ 7.84-7.80 (m, 4H, 2 molecules of benzensulfonic acid), 7.45-7.38 (m, 8H, 2 molecules of benzensulfonic acid + 2H), 7.34-7.29 (m, 2H), 7.26-7.22 (m, 1H), 6.99 (s, 2H), 6.51 (br d, J = 6.4 Hz, 1H), 4.00 (s, 6H), 3.32-3.20 (m, 8H), 2.87 (s, 3H), 2.60 (sept, J = 7.0 Hz, 1H), 2.46-2.27 (m, 4H), 2.06-1.97 (m, 1H), 1.95-1.91 (m, 1H), 1.76-1.69 (m, 2H), 1.49-1.40 (m, 1H), 1.29-1.22 (m, 1H), 1.19 (d, J = 2.9 Hz, 3H), 1.18 (d, J = 2.9 Hz, 3H). | Crystalline, see FIG. 9 |
| di-ethane sulfonic acid salt | 1H-NMR (MeOD, 400 MHz) δ 7.48-7.46 (m, 2H), 7.35-7.31 (m, 2H), 7.27-7.24 (m, 1H), 7.00 (s, 2H), 6.55 (dd, J = 7.0, 1.2 Hz, 1H), 4.01 (s, 6H), 3.22-3.15 (m, 8H), 2.87 (s, 3H), 2.79 (q, J = 7.8 Hz, 4 H, 2 molecules of ethane sulfonic acid), 2.62 (sept, J = 7.2 Hz, 1H), 2.50-2.29 (m, 4H), 2.07-1.94 (m, 2H), 1.80-1.71 (m, 2H), 1.50-1.41 (m, 1H), 1.29 (t, J = 7.8 Hz, 6H, 2 molecules of ethane sulfonic acid), 1.29-1.27 (m, 1H), 1.22 (d, J = 1.9 Hz, 3H), 1.19 (d, J = 2.4 Hz, 3H). | Crystalline, see FIG. 10 |
| di-naphthalene-2-sulfonic acid salt | 1H-NMR (MeOD, 400 MHz) δ 8.34 (br s, 2H, 2 molecules of naphthalene-2-sulfonic acid), 7.91-7.85 (m, 8H, 2 molecule of acid), 7.57-7.51 (m, 4H, 2 molecules of naphthalene-2-sulfonic acid), 7.38-7.35 (m, 2H), 7.39-7.19 (m, 3H), 6.88 (s, 2H), 6.44 (br d, J = 7.2 Hz, 1H), 3.95 (s, 6H), 3.31-3.10 (m, 8H), 2.87 (s, 3H), 2.58 (sept, J = 7.0 Hz, 1H), 2.47-2.25 (m, 4H), 2.04-1.94 (m, 1H), 1.93-1.86 (m, 1H), 1.74-1.64 (m, 2H), 1.46-1.36 (m, 1H), 1.27-1.19 (m, 1H), 1.18 (d, J = 1.6 Hz, 3H), 1.16 (d, J = 2.4 Hz, 3H). | Crystalline, see FIG. 11 |

TABLE 2

Characterisation data for further salt forms of COMPOUND
gained according to general procedure

| Salt | Technique |
|---|---|
| di-benzoic acid salt | 1H-NMR: Consistent with structure. |
| di-salicylic acid salt | 1H-NMR: Consistent with structure. |
| di-saccharinate | 1H-NMR: Consistent with structure. |
| di-malonic acid salt | 1H-NMR: Consistent with structure. |
| di-malic acid salt | 1H-NMR: Consistent with structure. |
| di-glycolic acid salt | 1H-NMR: Consistent with structure. |
| di-ketoglutaric acid salt | 1H-NMR: Consistent with structure. |
| di-phosphoric acid salt | Melting point at about 145° C. 1H-NMR consistent with structure. |
| di-citric acid salt | 1H-NMR: Consistent with structure. |
| di-succinic acid salt | 1H-NMR: Consistent with structure. |
| di-tartric acid salt | 1H-NMR: Consistent with structure. |

Reference Example S1

Preparation and Characterization of the Di-hydrochloric acid Salt of COMPOUND 7.598 mL aq. HCl (0.1N) was added to 200.7 mg COMPOUND resulting in a white suspension. 5 mL 2-PrOH were added and the obtained clear solution was evaporated to dryness under nitrogen. 4 mL TBME were added to the residue and the suspension was shaken with a temperature cycle (T1=20° C., T2=25° C., holding time 1 h, respectively; heating and cooling rate 5° C./h, 500 rpm). After 18 repetitions the suspension was filtered and the solid was dried in vacuum to yield 265 mg of the di-hydrochloric acid salt of COMPOUND.

TABLE S1

Characterisation data for the di-hydrochloric acid salt of COMPOUND

| Technique | Data Summary | Remarks |
|---|---|---|
| XRPD | Crystalline. The di-hydrochloride salt of COMPOUND is characterised by the presence of peaks in the X-ray powder diffraction diagram at the following angles of refraction 2θ: 9.19°, 9.77°, 15.36°, 16.14°, 17.08°, and 18.12° (especially characterised by 2θ: 9.19°, 9.77°, and 18.12°). | see FIG. 1 |
| Melting point | about 113° C. | |
| 1H-NMR | Consistent with structure. | |
| Elemental analysis | Consistent with di-hydrochloride salt | |

TABLE S1-continued

Characterisation data for the di-hydrochloric acid salt of COMPOUND

| Technique | Data Summary | Remarks |
| --- | --- | --- |
| Hygroscopicity | Slightly hygroscopic (mass change 0.5%) | |

Example S2

Preparation and Characterization of the Di-methanesulfonic Acid Salt of COMPOUND 0.0476 mL Methanesulfonic acid was added to a clear solution of 199.7 mg of COMPOUND dissolved in 7 ml EtOAc. The clear solution was evaporated to dryness under nitrogen and the obtained residue was suspended and shaken in 4 mL of a EtOAc/heptane (1:3) mixture with a temperature cycle (T1=20° C., T2=25° C., holding time 1 h, respectively; heating and cooling rate 5° C./h, 500 rpm). After 18 repetitions the suspension was filtered and the solid was dried in vacuum. The obtained solid was suspended and shaken in 1 mL TBME (temperature cycle: T1=20° C., T2=25° C., holding time 1 h, respectively; heating and cooling rate 5° C./h, 500 rpm). After 18 repetitions the suspension was filtered and the solid was dried in vacuum to yield the di-methanesulfonic acid salt of COMPOUND.

TABLE S2

Characterisation data for the di-methanesulfonic acid salt of COMPOUND

| Technique | Data Summary | Remarks |
| --- | --- | --- |
| XRPD | Crystalline | see FIG. 2 |
| $^1$H-NMR | 1H NMR (MeOD, 400 MHz) δ 7.48-7.46 (m, 2H), 7.35-7.32 (m, 2H), 7.27-7.23 (m, 1H), 7.00 (s, 2H), 6.57 (br d, J = 7.0 Hz, 1H), 4.01 (s, 6H), 3.35-3.20 (m, 8H), 2.89 (s, 3H), 2.71 (s, 6H, 2 molecules of methanesulfonic acid), 2.63 (sept, J = 7.2 Hz, 1H), 2.53-2.26 (m, 4H), 2.07-1.94 (m, 2H), 1.79-1.71 (m, 2H), 1.51-1.42 (m, 1H), 1.32-1.23 (m, 1H), 1.21 (d, J = 2.4 Hz, 3H), 1.20 (d, J = 1.8 Hz, 3H). | |
| Elemental analysis | Consistent with di-methanesulfonic acid salt. | |

Example S3

Preparation and Characterization of the Di-para-toluenesulfonic Acid Salt of COMPOUND 199.7 mg of COMPOUND was dissolved in 7 mL EtOAc. 139.2 mg para-toluenesulfonic acid dissolved in 10 mL EtOAc was added. The clear solution was evaporated to dryness under nitrogen and the residue was suspended in 4 mL of a EtOAc/Hept (1:3) mixture, and shaken with a temperature cycle (temperature cycle: T1=20° C., T2=25° C., holding time 1 h, respectively; heating and cooling rate 5° C./h, 500 rpm). After 18 cycles the solvent was evaporated under vacuum and the solid residue was suspended in 2 ml EtOAc. After brief sonication (3 min) the suspension was shaken with a temperature cycle (temperature cycle: T1=20° C., T2=25° C., holding time 1 h, respectively; heating and cooling rate 5° C./h, 500 rpm). After 18 repetitions the suspension was filtered and the solid was dried in vacuum to yield 173.8 mg of the di-para-toluenesulfonic acid salt of COMPOUND.

TABLE S3

Characterisation data for the di-para-toluenesulfonic acid salt of COMPOUND

| Technique | Data Summary | Remarks |
| --- | --- | --- |
| XRPD | Crystalline | see FIG. 3 |
| $^1$H-NMR | 1H NMR (MeOD, 400 MHz) δ 7.71-7.68 (m, 4H, 2 molecules of TsOH), 7.45-7.42 (m, 2H, 2 molecules of TsOH), 7.34-7.30 (m, 2H, 2 molecules of TsOH), 7.27-7.25 (m, 1H), 7.21-7.19 (m, 4H), 7.00 (s, 2H), 6.35 (br d, J = 8.0 Hz, 1H), 4.00 (s, 6H), 3.23-3.15 (m, 8H), 2.87 (s, 3H), 2.60 (sept, J = 7.0 Hz, 1H), 2.36 (s, 6H, 2 molecules of TsOH), 2.36-2.29 (m, 4H), 2.01-1.98 (m, 1H), 1.97-1.91 (m, 1H), 1.75-1.69 (m, 2H), 1.49-1.41 (m, 1H), 1.32-1.23 (m, 1H), 1.20 (d, J = 2.9 Hz, 3H), 1.17 (d, J = 2.9 Hz, 3H). | |
| Elemental analysis | Consistent with di-para-toluenesulfonic salt. | |

Example S4

Preparation and Characterization of the Sulfuric Acid Salt of COMPOUND 0.733 mL aqueous sulfuric acid (0.5M) was added to a solution of 200.2 mg COMPOUND in 10 mL MEK resulting in a clear solution. After 2 days the obtained suspension was filtered and the solid was dried in vacuum for 1 h yielding the mono-sulfuric acid salt of COMPOUND containing about 6 equivalents of water.

TABLE S4

Characterisation data for the di-sulfuric acid salt of COMPOUND

| Technique | Data Summary | Remarks |
| --- | --- | --- |
| XRPD | Crystalline | see FIG. 4 |
| Elemental analysis | Consistent with mono-sulfuric acid salt (about 1.1 equivalents $H_2SO_4$ found). Contains about 6 equivalents of water. | |

Example S5

Preparation and Characterization of the Di-maleic Acid Salt of COMPOUND

Maleic acid (256 g, 2.2 mol, 2.1 eq), dissolved in MeOH (630 mL, 1.1 volumes) was added to a refluxing solution of COMPOUND (682 g, 84% w/w (NMR assay), 1.05 mol) in EtOAc (6.3 L, 11 volumes). The resulting mixture was stirred under reflux for 15 minutes and was then cooled to 65-68° C. within 30 minutes and seeded with 0.04% w/w of seeding crystals of di-maleic acid salt of COMPOUND (Seeding crystals were obtained after careful crystallisation using the same protocol.). The mixture was then cooled from 65-68° C. to 40° C. within 3 h. The obtained suspension was then cooled down to 20° C. over 1 h, filtered under 0.2 bar of nitrogen and rinsed with EtOAc (1500 mL 2.6 volumes). The obtained white solid was then dried under 1 atmosphere of nitrogen for 24 hours to yield 715 g (88%) of the di-maleic acid salt of COMPOUND.

TABLE S5

Characterisation data for the di-maleic acid salt of COMPOUND

| Technique | Data Summary | Remarks |
|---|---|---|
| XRPD | Crystalline | see FIG. 5 |
| DSC | Melt endotherm with melting point at about 147° C. | |
| ¹H-NMR | 1H NMR (MeOD, 400 MHz) δ 7.31-7.21 (m, 5H), 6.68 (s, 2 H), 6.38 (br d, J = 5.8 Hz, 1H), 6.27 (s, 4H, 2 molecules of maleic acid), 3.88 (s, 6H), 3.32-3.10 (m, 8H), 2.86 (s, 3H), 2.60 (sept, J = 7.0 Hz, 1H), 2.52-2.45 (m, 2H), 2.29-2.23 (m, 2H), 2.06-2.02 (m, 1H), 1.96 (dd, J = 14.2, 2.4 Hz, 1H), 1.76-1.69 (m, 2H), 1.48-1.39 (m, 1H), 1.29-1.21 (m, 1H), 1.19 (d, J = 2.5 Hz, 3H), 1.18 (d, J = 2.5 Hz, 3H). | |
| Elemental analysis | Consistent with di-maleic acid salt. | |
| Hygroscopicity | Non hygroscopic (mass change 0.1%) | |

Example S6

Preparation of the Sesqui-fumarate Salt of COMPOUND 199.5 mg of COMPOUND were dissolved in 5 mL EtOAc. A clear solution of 85.4 mg fumaric acid in 5 mL THF was slowly added. The obtained clear solution was concentrated to 3 mL solution under nitrogen resulting in precipitation. The mixture was filtered and the solid was dried in vacuum. The obtained solid was the sesqui-fumaric acid salt of COMPOUND.

TABLE S6

Characterisation data for the sesqui-fumaric acid salt of COMPOUND

| Technique | Data Summary | Remarks |
|---|---|---|
| XRPD | Crystalline | see FIG. 6 |
| DSC | Melt endotherm with melting point at about 180° C. | |
| ¹H-NMR | 1H NMR (MeOD, 400 MHz) δ 7.25-7.20 (m, 5H), 6.73 (s, 3 H, 1.5 molecule of fumaric acid), 6.59 (s, 2H), 6.35 (dd, J = 7.1, 1.6 Hz, 1H), 3.86 (s, 6H), 3.29-3.22 (m, 4H), 3.22-3-18 (m, 1H), 3.15-3.11 (m, 3H), 2.85 (s, 3H), 2.60 (sept, J = 7.0 Hz, 1H), 2.53-2.46 (m, 2H), 2.28-2.21 (m, 2H), 2.07-1.98 (m, 1H), 1.96 (dd, J = 14.0, 2.8 Hz, 1H), 1.76-1.69 (m, 2H), 1.48-1.39 (m, 1H), 1.29-1.21 (m, 1H), 1.19 (d, J = 2.8 Hz, 3H), 1.18 (d, J = 2.8 Hz, 3H). | |
| Elemental analysis | Consistent with sesqui-fumaric acid salt. | |
| Hygroscopicity | Non hygroscopic (mass change 0.1%) | |

Example S7

Preparation of the Di-hydrobromic Acid Salt of COMPOUND 0.3665 mL of aqueous 2 molar hydrobromic acid was slowly added to a solution of 199.8 mg COMPOUND in 0.4 ml THF and the obtained suspension was heated (heat gun). The clear solution was cooled to r.t. resulting in a precipitation. 3 mL THF was added, the suspension was shaken, filtered and the solid was vacuum dried (1 h, 3 mbar). The obtained solid was the di-hydrobromic acid salt of COMPOUND containing about 3 equivalents of water.

TABLE S7

Characterisation data for the di-hydrobromic acid salt of COMPOUND

| Technique | Data Summary | Remarks |
|---|---|---|
| XRPD | Crystalline | see FIG. 7 |
| DSC | 2 broad endotherms with peaks at about 99 and 117° C. | |
| Elemental analysis | Consistent with di-hydrobromic acid salt. Contains about 3 equivalents of water. | |
| Hygroscopicity | Non hygroscopic (mass change 0.1%) | |

The invention claimed is:

1. A crystalline salt of the compound isobutyric acid (1R*,2R*,4R*)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester,
wherein said crystalline salt consists of:
1 equivalent of compound isobutyric acid (1R*,2R*,4R*)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester;
2 equivalents of maleic acid; and
0 equivalents of water;
characterised by the presence of peaks in the X-ray powder diffraction diagram at the following angles of refraction 2θ: 10.15°, 20.39°, and 22.63°; wherein said X-ray powder diffraction diagram is obtained by using Cu Kα1 radiation; and the accuracy of the 2θ values is in the range of 2θ+/−0.2°;
or said crystalline salt consists of:
1 equivalent of isobutyric acid (1R*,2R*,4R*)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester;
an acid component consisting of 1.5 equivalents of fumaric acid; and
0 to 5 equivalents of water.
characterised by the presence of peaks in the X-ray powder diffraction diagram at the following angles of refraction 2θ: 5.27°, 8.05°, and 20.61°; wherein said X-ray powder diffraction diagram is obtained by using Cu Kα1 radiation; and the accuracy of the 2θ values is in the range of 2θ+/−0.2°,
or said crystalline salt consists of:
1 equivalent of isobutyric acid (1R*,2R*,4R*)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester;
an acid component consisting of 2 equivalents of hydrobromic acid; and
0 to 5 equivalents of water;
characterised by the presence of peaks in the X-ray powder diffraction diagram at the following angles of refraction 2θ: 9.3°, 15.6°, and 17.3°; wherein said X-ray powder diffraction diagram is obtained by using Cu Kα1 radiation; and the accuracy of the 2θ values is in the range of 2θ+/−0.2°.

2. The crystalline salt of the compound isobutyric acid (1R*,2R*,4R*)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester according to claim 1, wherein said crystalline salt consists of:

1 equivalent of isobutyric acid (1R*,2R*,4R*)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester;

2 equivalents of maleic acid; and 0 equivalents of water;

characterised by the presence of peaks in the X-ray powder diffraction diagram at the following angles of refraction 2θ: 10.15 °, 20.39°, and 22.63°; wherein said X-ray powder diffraction diagram is obtained by using Cu Kα1 radiation; and the accuracy of the 2θ values is in the range of 2θ+/−0.2°.

3. The crystalline salt of the compound isobutyric acid (1R*,2R*,4R*)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester according to claim 2, characterised by the presence of peaks in the X-ray powder diffraction diagram at the following angles of refraction 2θ: 5.07°, 8.19°, 10.15°, 15.26°, 17.61°, 20.39°, 22.63°, 23.93°, 24.27°, and 25.61°; wherein said X-ray powder diffraction diagram is obtained by using Cu Kα1 radiation; and the accuracy of the 2θ values is in the range of 2θ+/−0.2°.

4. The crystalline salt of the compound isobutyric acid (1R*,2R*,4R*)-2-(2{[3-(4,7-dimethoxy-1H-benzoimidazol-2-yl)-propyl]-methyl-amino}-ethyl)-5-phenyl-bicyclo[2.2.2]oct-5-en-2-yl ester according to claim 1, wherein said crystalline salt consists of:

1 equivalent of isobutyric acid (1R*,2R*,4R*)-2-(2{[3-(4,7-dimethoxy-1H-benzoimidazol-2-yl)-propyl]-methyl-amino}-ethyl)-5-phenyl-bicyclo[2.2.2]oct-5-en-2-yl ester;

an acid component consisting of 1.5 equivalents of fumaric acid; and 0 to 5 equivalents of water;

characterised by the presence of peaks in the X-ray powder diffraction diagram at the following angles of refraction 2θ: 5.27°, 8.05°, and 20.61°; wherein said X-ray powder diffraction diagram is obtained by using Cu Kα1 radiation; and the accuracy of the 2θ values is in the range of 2θ+/−0.2°.

5. The crystalline salt of the compound isobutyric acid (1R*,2R*,4R*)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester according to claim 1, wherein said crystalline salt consists of:

1 equivalent of isobutyric acid (1R*,2R*,4R*)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester;

an acid component consisting of 2 equivalents of hydrobromic acid; and 0 to 5 equivalents of water;

characterised by the presence of peaks in the X-ray powder diffraction diagram at the following angles of refraction 2θ: 9.3°, 15.6°, and 17.3°; wherein said X-ray powder diffraction diagram is obtained by using Cu Kα1 radiation; and the accuracy of the 2θ values is in the range of 2θ+/−0.2°.

6. A pharmaceutical composition comprising a crystalline salt of the compound isobutyric acid (1R*,2R*,4R*)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester as defined in claim 1, and a pharmaceutically acceptable carrier.

7. The pharmaceutical composition according to claim 6, wherein said compound is enantiomerically enriched isobutyric acid (1R*,2R*,4R*)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester.

8. A method of treatment of a disease or disorder associated with abnormal elevated calcium influx through the plasma membrane of the cardiac and vascular smooth muscle cells comprising administering to a subject in need thereof an effective amount of the pharmaceutical composition according to claim 6, wherein said disease or disorder is selected from the group consisting of: chronic stable angina, hypertension, ischemia, renal ischemia, cardiac ischemia, cardiac arrhythmias, atrial fibrillation, cardiac hypertrophy, and congestive heart failure.

9. A pharmaceutical composition comprising a crystalline salt of the compound isobutyric acid (1R*,2R*,4R*)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester as defined in claim 2, and a pharmaceutically acceptable carrier.

10. A pharmaceutical composition comprising a crystalline salt of the compound isobutyric acid (1R*,2R*,4R*)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester as defined in claim 3, and a pharmaceutically acceptable carrier.

11. The pharmaceutical composition according to claim 9, wherein said compound is enantiomerically enriched isobutyric acid (1R*,2R*,4R*)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester.

12. The pharmaceutical composition according to claim 10, wherein said compound is enantiomerically enriched isobutyric acid (1R*,2R*,4R*)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester.

13. A method of treatment of a disease or disorder associated with abnormal elevated calcium influx through the plasma membrane of the cardiac and vascular smooth muscle cells comprising administering to a subject in need thereof an effective amount of the pharmaceutical composition according to claim 9, wherein said disease or disorder is selected from the group consisting of chronic stable angina, hypertension, renal ischemia, cardiac ischemia, cardiac arrhythmias, atrial fibrillation, cardiac hypertrophy, and congestive heart failure.

* * * * *

UNITED STATES PATENT AND TRADEMARK OFFICE
CERTIFICATE OF CORRECTION

PATENT NO. : 8,492,555 B2  Page 1 of 1
APPLICATION NO. : 13/125443
DATED : July 23, 2013
INVENTOR(S) : Abele et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 77 days.

Signed and Sealed this
Eighth Day of September, 2015

Michelle K. Lee
*Director of the United States Patent and Trademark Office*

UNITED STATES PATENT AND TRADEMARK OFFICE
CERTIFICATE OF CORRECTION

PATENT NO. : 8,492,555 B2  
APPLICATION NO. : 13/125443  
DATED : July 23, 2013  
INVENTOR(S) : Abele et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 118 days.

This certificate supersedes the Certificate of Correction issued September 8, 2015.

Signed and Sealed this  
Fifth Day of April, 2016

Michelle K. Lee  
*Director of the United States Patent and Trademark Office*